US 8,974,463 B2

(12) United States Patent
Pool et al.

(10) Patent No.: US 8,974,463 B2
(45) Date of Patent: Mar. 10, 2015

(54) NON-INVASIVE ADJUSTABLE DISTRACTION SYSTEM

(75) Inventors: Scott Pool, Laguna Hills, CA (US); Blair Walker, Mission Viejo, CA (US)

(73) Assignee: Ellipse Technologies, Inc., Irvine, CA (US)

( * ) Notice: Subject to any disclaimer, the term of this patent is extended or adjusted under 35 U.S.C. 154(b) by 25 days.

(21) Appl. No.: 13/477,945

(22) Filed: May 22, 2012

(65) Prior Publication Data

US 2012/0232559 A1 Sep. 13, 2012

Related U.S. Application Data

(63) Continuation of application No. 12/391,109, filed on Feb. 23, 2009, now Pat. No. 8,197,490.

(51) Int. Cl.
*A61B 17/58* (2006.01)
*A61B 17/60* (2006.01)
(Continued)

(52) U.S. Cl.
CPC ......... *A61B 17/7004* (2013.01); *A61B 17/7016* (2013.01); *A61B 17/707* (2013.01); *A61B 17/7011* (2013.01); *A61B 2017/00199* (2013.01); *A61B 2017/00212* (2013.01); *A61B 2017/00411* (2013.01)
USPC ................ 606/90; 606/57; 606/282; 606/105

(58) Field of Classification Search
CPC ...... A61B 17/60; A61B 17/66; A61B 17/663; A61B 17/666; A61B 2017/025; A61B 2017/60; A61B 2017/681
USPC ...................... 606/53, 90, 105, 246, 249, 279
See application file for complete search history.

(56) References Cited

U.S. PATENT DOCUMENTS

| 2,702,031 A | 2/1955 | Wenger |
| 3,372,476 A | 3/1968 | Peiffer et al. |

(Continued)

FOREIGN PATENT DOCUMENTS

| CA | 2655093 | 12/2007 |
| CA | 2655093 A1 | 12/2007 |

(Continued)

OTHER PUBLICATIONS

U.S. Appl. No. 11/654,068, filed Jan. 16, 2007.
(Continued)

*Primary Examiner* — Kevin T Truong
*Assistant Examiner* — Samuel Hanna
(74) *Attorney, Agent, or Firm* — Knobbe, Martens, Olson & Bear LLP

(57) ABSTRACT

A spinal distraction system includes a distraction rod having a first end and a second end, the first end being configured for affixation to a subject's spine at a first location, the distraction rod having a second end containing a recess having a threaded portion disposed therein. The system further includes an adjustable portion configured for affixation relative to the subject's spine at a second location remote from the first location, the adjustable portion comprising a housing containing a magnetic assembly, the magnetic assembly affixed at one end thereof to a lead screw, the lead screw operatively coupled to the threaded portion. A locking pin may secure the lead screw to the magnetic assembly. An o-ring gland disposed on the end of the housing may form a dynamic seal with the distraction rod.

14 Claims, 15 Drawing Sheets

(51) Int. Cl.
*A61F 2/00* (2006.01)
*A61B 17/70* (2006.01)
*A61B 17/00* (2006.01)

(56) References Cited

U.S. PATENT DOCUMENTS

| | | | |
|---|---|---|---|
| 3,397,928 A | 8/1968 | Galle | |
| 3,597,781 A | 8/1971 | Eibes et al. | |
| 3,810,259 A | 5/1974 | Summers | |
| 3,976,060 A | 8/1976 | Hildebrandt et al. | |
| 4,068,821 A | 1/1978 | Morrison | |
| 4,078,559 A | 3/1978 | Nissinen | |
| 4,448,191 A | 5/1984 | Rodnyansky et al. | |
| 4,658,809 A | 4/1987 | Ulrich | |
| 4,854,304 A | 8/1989 | Zielke | |
| 5,010,879 A | 4/1991 | Moriya et al. | |
| 5,030,235 A | 7/1991 | Campbell, Jr. | |
| 5,064,004 A | 11/1991 | Lundell | |
| 5,092,889 A | 3/1992 | Campbell, Jr. | |
| 5,261,908 A | 11/1993 | Campbell, Jr. | |
| 5,263,955 A | 11/1993 | Baumgart et al. | |
| 5,290,289 A | 3/1994 | Sanders et al. | |
| 5,466,261 A | 11/1995 | Richelsoph | |
| 5,468,030 A * | 11/1995 | Walling | 285/364 |
| 5,575,790 A | 11/1996 | Chen et al. | |
| 5,626,579 A | 5/1997 | Muschler et al. | |
| 5,632,744 A | 5/1997 | Campbell, Jr. | |
| 5,672,175 A | 9/1997 | Martin | |
| 5,704,939 A | 1/1998 | Justin | |
| 5,720,746 A | 2/1998 | Soubeiran | |
| 5,743,910 A | 4/1998 | Bays et al. | |
| 5,800,434 A | 9/1998 | Campbell, Jr. | |
| 5,961,553 A | 10/1999 | Coty et al. | |
| 6,033,412 A | 3/2000 | Losken et al. | |
| 6,106,525 A | 8/2000 | Sachse | |
| 6,200,317 B1 | 3/2001 | Aalsma et al. | |
| 6,283,156 B1 | 9/2001 | Motley | |
| 6,336,929 B1 | 1/2002 | Justin | |
| 6,358,283 B1 | 3/2002 | Hogfors et al. | |
| 6,409,175 B1 | 6/2002 | Evans et al. | |
| 6,417,750 B1 | 7/2002 | Sohn | |
| 6,765,330 B2 | 7/2004 | Baur | |
| 6,796,984 B2 | 9/2004 | Soubeiran | |
| 6,835,207 B2 | 12/2004 | Zacouto et al. | |
| 6,849,076 B2 | 2/2005 | Blunn et al. | |
| 6,918,910 B2 | 7/2005 | Smith et al. | |
| 7,029,472 B1 | 4/2006 | Fortin | |
| 7,135,022 B2 | 11/2006 | Kosashvili et al. | |
| 2003/0144669 A1 | 7/2003 | Robinson | |
| 2004/0193266 A1 | 9/2004 | Meyer | |
| 2005/0034705 A1 | 2/2005 | McClendon | |
| 2005/0049617 A1 | 3/2005 | Chatlynne et al. | |
| 2005/0055025 A1 | 3/2005 | Zacouto et al. | |
| 2005/0065529 A1 | 3/2005 | Liu et al. | |
| 2005/0234448 A1 | 10/2005 | McCarthy | |
| 2005/0246034 A1 | 11/2005 | Soubeiran | |
| 2005/0251109 A1 | 11/2005 | Soubeiran | |
| 2005/0261779 A1 | 11/2005 | Meyer | |
| 2006/0004459 A1 | 1/2006 | Hazebrouck et al. | |
| 2006/0009767 A1 | 1/2006 | Kiester | |
| 2006/0036323 A1 | 2/2006 | Carl et al. | |
| 2006/0036324 A1 | 2/2006 | Sachs et al. | |
| 2006/0047282 A1 | 3/2006 | Gordon | |
| 2006/0052782 A1 | 3/2006 | Morgan et al. | |
| 2006/0058792 A1 | 3/2006 | Hynes | |
| 2006/0069447 A1 | 3/2006 | DiSilvestro et al. | |
| 2006/0074448 A1 | 4/2006 | Harrison et al. | |
| 2006/0079897 A1 | 4/2006 | Harrison et al. | |
| 2006/0136062 A1 | 6/2006 | DiNello et al. | |
| 2006/0155279 A1 | 7/2006 | Ogilvie | |
| 2006/0195087 A1 | 8/2006 | Sacher et al. | |
| 2006/0195088 A1 | 8/2006 | Sacher et al. | |
| 2006/0241767 A1 * | 10/2006 | Doty | 623/17.12 |
| 2006/0249914 A1 * | 11/2006 | Dulin | 277/512 |
| 2006/0271107 A1 | 11/2006 | Harrison et al. | |
| 2007/0010887 A1 | 1/2007 | Williams et al. | |
| 2007/0050030 A1 | 3/2007 | Kim | |
| 2007/0161984 A1 | 7/2007 | Cresina et al. | |
| 2007/0173837 A1 | 7/2007 | Chan et al. | |
| 2007/0179493 A1 | 8/2007 | Kim | |
| 2007/0213751 A1 | 9/2007 | Scirica et al. | |
| 2007/0233098 A1 | 10/2007 | Mastrorio et al. | |
| 2007/0239161 A1 | 10/2007 | Giger et al. | |
| 2007/0255088 A1 | 11/2007 | Jacobson et al. | |
| 2007/0270803 A1 | 11/2007 | Giger et al. | |
| 2007/0276368 A1 | 11/2007 | Trieu et al. | |
| 2007/0276369 A1 | 11/2007 | Allard et al. | |
| 2007/0276378 A1 * | 11/2007 | Harrison et al. | 606/61 |
| 2007/0288024 A1 | 12/2007 | Gollogly | |
| 2008/0009792 A1 | 1/2008 | Henniges et al. | |
| 2008/0027436 A1 | 1/2008 | Cournoyer et al. | |
| 2008/0033436 A1 | 2/2008 | Song et al. | |
| 2008/0048855 A1 | 2/2008 | Berger | |
| 2008/0190237 A1 | 8/2008 | Radinger et al. | |
| 2009/0030462 A1 | 1/2009 | Buttermann | |
| 2009/0275984 A1 | 11/2009 | Kim et al. | |

FOREIGN PATENT DOCUMENTS

| | | |
|---|---|---|
| DE | 8515687 | 12/1985 |
| DE | 102005045070 | 4/2007 |
| DE | 102005045070 A1 | 4/2007 |
| FR | 2900563 | 11/2007 |
| FR | 2900563 A1 | 11/2007 |
| FR | 2901991 | 12/2007 |
| FR | 2901991 A1 | 12/2007 |
| JP | 09-056736 | 3/1997 |
| WO | WO 99/51160 | 10/1999 |
| WO | WO 99/51160 A1 | 10/1999 |
| WO | WO 01/67973 | 9/2001 |
| WO | WO 01/78614 | 10/2001 |
| WO | WO 2006/090380 | 8/2006 |
| WO | WO 2006/090380 A2 | 8/2006 |
| WO | WO 2007/015239 | 2/2007 |
| WO | WO 2007/015239 A2 | 2/2007 |
| WO | WO 2007/025191 | 3/2007 |
| WO | WO 2007/025191 A1 | 3/2007 |
| WO | WO 2007/118179 | 10/2007 |
| WO | WO 2007/118179 A2 | 10/2007 |
| WO | WO 2007/144489 | 12/2007 |
| WO | WO 2007/144489 A2 | 12/2007 |
| WO | WO 2008/003952 | 1/2008 |
| WO | WO 2008/003952 A1 | 1/2008 |
| WO | WO 2008/040880 | 4/2008 |
| WO | WO 2008/040880 A2 | 4/2008 |

OTHER PUBLICATIONS

U.S. Appl. No. 11/796,052, filed Apr. 27, 2007.
U.S. Appl. No. 11/888,537, filed Jul. 31, 2007.
U.S. Appl. No. 11/732,431, filed Apr. 2, 2007.
U.S. Appl. No. 11/760,482, filed Jun. 8, 2007.
U.S. Appl. No. 12/259,965, filed Oct. 28, 2008.
U.S. Appl. No. 13/158,117, filed Jun. 10, 2011.
U.S. Appl. No. 11/760,488, filed Jun. 8, 2007.
U.S. Appl. No. 11/779,818, filed Jul. 18, 2007.
U.S. Appl. No. 12/121,355, filed May 15, 2008.
U.S. Appl. No. 12/121,438, filed May 15, 2008.
U.S. Appl. No. 12/121,499, filed May 15, 2008.
U.S. Appl. No. 13/277,980, filed Oct. 20, 2011.
U.S. Appl. No. 12/250,442, filed Oct. 13, 2008.
U.S. Appl. No. 12/250,454, filed Oct. 13, 2008.
U.S. Appl. No. 12/250,456, filed Oct. 13, 2008.
U.S. Appl. No. 12/250,459, filed Oct. 13, 2008.
U.S. Appl. No. 12/250,464, filed Oct. 13, 2008.
Abe, J., Nagata, K., Ariyoshi, M., Inoue, A., "Experimental External Fixation Combined with Pecutaneous Discectomy in the Management of Scoliosis", Spine, 1999, vol. 24, No. 7, pp. 646-653, Lippincott Co., Philadelphia, U.S.A.

(56) References Cited

OTHER PUBLICATIONS

Buchowski, J., Bhatnagar, R., Skaggs, D., Sponseller, P., "Temporary Internal Distraction as an Aid to Correction of Severe Scoliosis", Journal of Bone and Joint Surgery American Edition, 2006, vol. 88A, No. 9, pp. 2035-2041, Journal of Bone and Joint Surgery, Boston, U.S.A.

Buchowski, J., Skaggs, D., Sponseller, P., "Temporary Internal Distraction as an Aid to Correction of Severe Scoliosis. Surgical Technique", Journal of Bone and Joint Surgery American Edition, 2007, vol. 89A No. Supp. 2 (Pt. 2), pp. 297-309, Journal of Bone and Joint Surgery, Boston, U.S.A.

Burke, J., "Design of a Minimally Invasive Non Fusion Device for the Surgical Management of Scoliosis in the Skeletally Immature", Studies in Health Technology and Informatics, 2006, vol. 123, pp. 378-384, IOS Press, Amsterdam, The Netherlands.

Cole, J., Paley, D., Dahl, M., "Operative Technique. ISKD. Intramedullary Skeletal Kinetic Distractor. Tibial Surgical Technique" IS-0508(A)-OPT-US © Orthofix Inc. Nov. 2005.

Daniels, A., Gemperline, P., Grahn, A., Dunn, H., "A New Method for Continuous Intraoperative Measurement of Harrington Rod Loading Patterns", Annals of Biomedical Engineering, 1984, vol. 12, No. 3, pp. 233-246, Dordrecht Kluwer Academic/Plenum Publishers, New York, U.S.A.

Edelan, H., Eriksson, G., Dahlberg, E., "Instrument for distraction by limited surgery in scoliosis treatment", Journal of Biomedical Engineering, 1981, vol. 3, No. 2, pp. 143-146, Butterfield Scientific Limited, Guilford, England.

Ember, T., Noordeen, H., "Distraction forces required during growth rod lengthening", Journal of Bone and Joint Surgery British Edition, 2006, vol. 88B, No. Supp. II, p. 229, Churchill Livingstone, London, England.

Gao et al., CHD7 Gene Polymorphisms Are Associated with Susceptibility to Idiopathic Scoliosis, American Journal of Human Genetics, vol. 80, pp. 957-967 (May 2007).

Gebhart, M., Neel, M., Soubeiran, A., Dubousset, J., "Early clinical experience with a custom made growing endoprosthesis in children with malignant bone tumors of the lower extremity actioned by an external permanent magnet: the Phenix M system", International Society of Limb Salvage 14th International Symposium on Limb Salvage, Sep. 13, 2007, Hamburg, Germany.

Gillespie, R., O'Brien, J., "Harrington Instrumentation without Fusion", The Journal of Bone and Joint Surgery British Edition, 1981, vol. 63B, No. 3, p. 461, Churchill Livingstone, London, England.

Grass, P., Soto, A., Araya, H., "Intermittent Distracting Rod for Correction of High Neurologic Risk Congenital Scoliosis", Spine, 1997, vol. 22, No. 16, pp. 1922-1927, Lippincott Co., Philadelphia, U.S.A.

Grimer, R., Chotel, F., Abudu, S., Tillman, R., Carter, S., "Non-invasive extendable endoprosthesis for childern—expensive but worth it", International Society of Limb Salvage 14th International Symposium on Limb Salvage, Sep. 13, 2007, Hamburg, Germany.

Guichet, J., Deromedis, B., Donnan, L., Peretti, G., Lascombes, P., Bado,F., "Gradual Femoral Lengthening with the Albizzia Intramedullary Nail", Journal of Bone and Joint Surgery American Edition, 2003, vol. 85, pp. 838-848. (12 pages).

Gupta, A., Meswania, J., Pollock, R., Cannon, S., Briggs, T., Taylor, S., Blunn, G., "Non-Invasive Distal Femoral Expandable Endoprosthesis for Limb-Salvage Surgery in Paediatric Tumours", The Journal of Bone and Joint Surgery British Edition, 2006, vol. 88-B, No. 5, pp. 649-654, Churchill Livingstone, London, England.

Hankemeier, S., Gosling, T., Pape, H., Wiebking, U., Krettek, C., "Limb Lengthening with the Intramedullary Skeletal Kinetic Distractor (ISKD)", Operative Orthopadie und Traumatologie, 2005, vol. 17, No. 1, pp. 79-101, Urban & Vogel, Munich, Germany.

Harrington, P., "Treatment of Scoliosis: Correction and Internal Fixation by Spine Instrumentation", The Journal of Bone and Joint Surgery American Edition, 1962, vol. 44A, No. 4, pp. 591-610, Journal of Bone and Joint Surgery, Boston, U.S.A.

Hazem Elsebaie M.D., Single Growing Rods (Review of 21 cases). Changing the Foundations: Does it affect the Results?, J. Child Orthop. (2007) 1:258.

Klemme, W., Denis, F., Winter, R., Lonstein, J., Koop, S., "Spinal Instrumentation without Fusion for Progressive Scoliosis in Young Childern", Journal of Pediatric Orthopedics. 1997, vol. 17, No. 6, pp. 734-742, Raven Press, New York, U.S.A.

Lonner, B., "Emerging minimally invasive technologies for the management of scoliosis", Orthopedic Clinics of North America, 2007; vol. 38, No. 3, pp. 431-440, Saunders, Philadelphia, U.S.A.

Marco Teli, M.D. et al., Measurement of Forces Generated During Distraction of Growing Rods. Marco Teli, J. Child Orthop. (2007) 1:257-258.

Mineiro, J., Weinstein, S., "Subcutaneous Rodding for Progressive Spinal Curvatures: Early Results", Journal of Pediatric Orthopedics, 2002, vol. 22, No. 3, pp. 290-295, Raven Press, New York, U.S.A.

Moe, J., Kharrat, K., Winter, R., Cummine, J., "Harrington Instrumentation without Fusion Plus External Orthotic Support for the Treatment of Difficult Curvature Problems in Young Children", Clinical Orthopaedics and Related Research, 1984, No. 185. pp. 35-45, Lippincott Co., Philadelphia, U.S.A.

Nachemson, A., Elfstrom, G., "Intravital Wireless Telemetry of Axial Forces in Harrington Distraction Rods In Patients with Idiopathic Scoliosis", The Journal of Bone and Joint Surgery American Edition, 1971, vol. 53A, No. 3, pp. 445-465, Journal of Bone and Joint Surgery, Boston, U.S.A.

Nachlas, I., Borden, J., "The cure of experimental scoliosis by directed growth control". The Journal of Bone and Joint Surgery American Edition, 1951, vol. 33, No. A:1, pp. 24-34, Journal of Bone and Joint Surgery, Boston, U.S.A.

Newton, P., "Fusionless Scoliosis Correction by Anterolateral Tethering . . . Can it Work?", 39th Annual Scoliosis Research Society Meeting, Sep. 6, 2004, Buenos Aires, Argentina (transcript and slides supplied).

PCT International Preliminary Report on Patentability (Chapter I of the Patent Cooperation Treaty) for PCT/US2010/023780, Applicant: Ellipse Technologies, Inc., Form PCT/IB/326 and 373, dated Sep. 1, 2011 (7pages).

PCT International Search Report for PCT/US2010/023780, Applicant: Ellipse Technologies, Inc., Form PCT/ISA/210 and 220, dated Apr. 16, 2010 (4 pages).

PCT Written Opinion of the International Search Authority for PCT/US2010/023780, Applicant: Ellipse Technologies, Inc., Form PCT/ISA/237, dated Apr. 16, 2010 (5 pages).

Rathjen, K., Wood, M., McClung, A., Vest, Z., "Clinical and Radiographic Results after Implant Removal in Idiopathic Scoliosis", Spine, 2007, vol. 32, No. 20, pp. 2184-2188, Lippincott Co., Philadelphia, U.S.A.

Reyes-Sanchez, A., Rosales, L., Miramontes, V., "External Fixation for Dynamic Correction of Severe Scoliosis", The Spine Journal, 2005, vol.5, No. 4, pp. 418-426, Elsevier Science Inc., New York, U.S.A.

Rinsky, L., Gamble, J., Bleck, E., "Segmental Instrumentation Without fusion In Children with Progressive Scoliosis", Journal of Pediatric Orthopedics, 1985, vol. 5, No. 6, pp. 687-690, Raven Press, New York, U.S.A.

Schmerling, M., Wilkov, M., Sanders, A., "Using the Shape Recovery of Nitinol in the Harrington Rod Treatment of Scoliosis", Journal of Biomedical Materials Research, 1976, vol. 10, No. 6, pp. 879-892, Wiley, Hoboken, U.S.A.

Sharke, P., "The Machinery of Life", Mechanical Engineering Magazine, Feb, 2004, Printed from Internet site Oct. 24, 2007 http://www.memagazine.org/contents/current/features/moflife/moflife.html.

Smith J., "The Use of Growth-Sparing Instrumentation in Pediatric Spinal Deformity", Orthopedic Clinics of North America, 2007, vol. 38, No. 4, pp. 547-552, Saunders, Philadelphia, U.S.A.

Soubeiran, A., Gebhart, M., Miladi, L., Griffet, J., Neel, M., Dubousset, J., "The Phenix M system, a fully implanted non-invasive lengthening device externally controllable through the skin with a palm size permanent magnet. Applications in limb salvage." International Society of Limb Salvage 14th International Symposium on Limb Salvage, Sep. 13, 2007, Hamburg, Germany.

Soubeiran. A., Gebhart, M., Miladi, L., Griffet, J., Neel, M., Dubousset, J., "The Phenix M System. A Mechanical Fully Implanted Lengthening Device Externally Controllable Through the Skin with a Palm Size Permanent Magnet; Applications to Pediatric

(56) References Cited

OTHER PUBLICATIONS

Orthopaedics", 6th European Research Conference in Pediatric Orthopaedics, Oct. 6, 2006, Toulouse, France.

Takaso, M., Moriya, H., Kitahara, H., Minami, S., Takahashi, K., Isobe, K., Yamagata, M., Otsuka, Y., Nakata, Y., Inoue, M., "New remote-controlled growing-rod spinal instrumentation possibly applicable for scoliosis in young children", Journal of Orthopaedic Science, 1998, vol. 3, No. 6, pp. 336-340, Springer-Verlag, Tokyo, Japan.

Teli, Marco, M.D., et al., Measurement of Forces Generated During Distraction of Growing Rods, J. Child Orthop., 1:257-258 (2007).

Tello C., "Harrington Instrumentation without Arthrodesis and Consecutive Distraction Program for Young Children with Severe Spinal Deformities: Experience and Technical Details", Orthopedic Clinics of North America, vol. 25, No. 2 1994. pp. 333-351. (19 pages).

Thompson, G., Akbarnia, B., Campbell, R., "Growing Rod Techniques in Early-Onset Scoliosis", Journal of Pediatric Orthopedics, 2007, vol. 27, No. 3, pp. 354-361, Raven Press, New York, U.S.A.

Thompson, G., Lenke, L., Akbarnia, B., McCarthy, R., Campbell, Jr., R., "Early Onset Scoliosis: Future Directions", 2007, Journal of Bone and Joint Surgery American Edition, vol. 89A, No. Supp. 1, pp. 163-166, Journal of Bone and Joint Surgery, Boston, U.S.A.

Trias, A., Bourassa, P., Massoud, M., "Dynamic Loads Experienced in Correction of Idiopathic Scoliosis Using Two Types of Harrington Rods", Spine, 1979, vol. 4, No. 3, pp. 228-235, Lippincott Co., Philadelphia, U.S.A.

Verkerke, G., Koops, H., Veth, R., Grootenboer, H., De Boer, L., Oldhoff, J., Postma, A. "Development and Test of an Extendable Endoprosthesis for Bone Reconstruction in the Leg", The International Journal of Artificial Organs, 1994, vol. 17, No. 3, pp. 155-162, Wichtig Editore, Milan, Italy.

Verkerke, G., Koops, H., Veth, R., Oldhoff, J., Nielsen, H., vanden Kroonenberg, H., Grootenboer, H., van Krieken, F., "Design of a Lengthening Element for a Modular Femur Endoprosthetic System", Proceedings of the Institution of Mechanical Engineers Part H: Journal of Engineering in Medicine, 1989, vol. 203, No. 2, pp. 97-102, Mechanical Engineering Publications, London, England.

Verkerke, G., Koops, H., Veth, R., van den Kroonenberg, H., Grootenboer, H., Nielsen, H., Oldhoff, J., Postma, A., "An Extendable Modular Endoprosthetic System for Bone Tumour Management in the Leg", Journal of Biomedical Engineering, 1990, vol. 12, No. 2, pp. 91-96, Butterfield Scientific Limited, Guilford, England.

Wenger, H., "Spine Jack Operation in the Correction of Scoliotic Deformity", Archives of Surgery, 1961, vol. 83, pp. 123-132 (901-910), American Medical Association, Chicago, U.S.A.

White, A., Panjabi, M., "The Clinical Biomechanics of Scoliosis", Clinical Orthopaedics and Related Research, 1976, No. 118, pp. 100-112, Lippincott Co., Philadelphia, U.S.A.

* cited by examiner

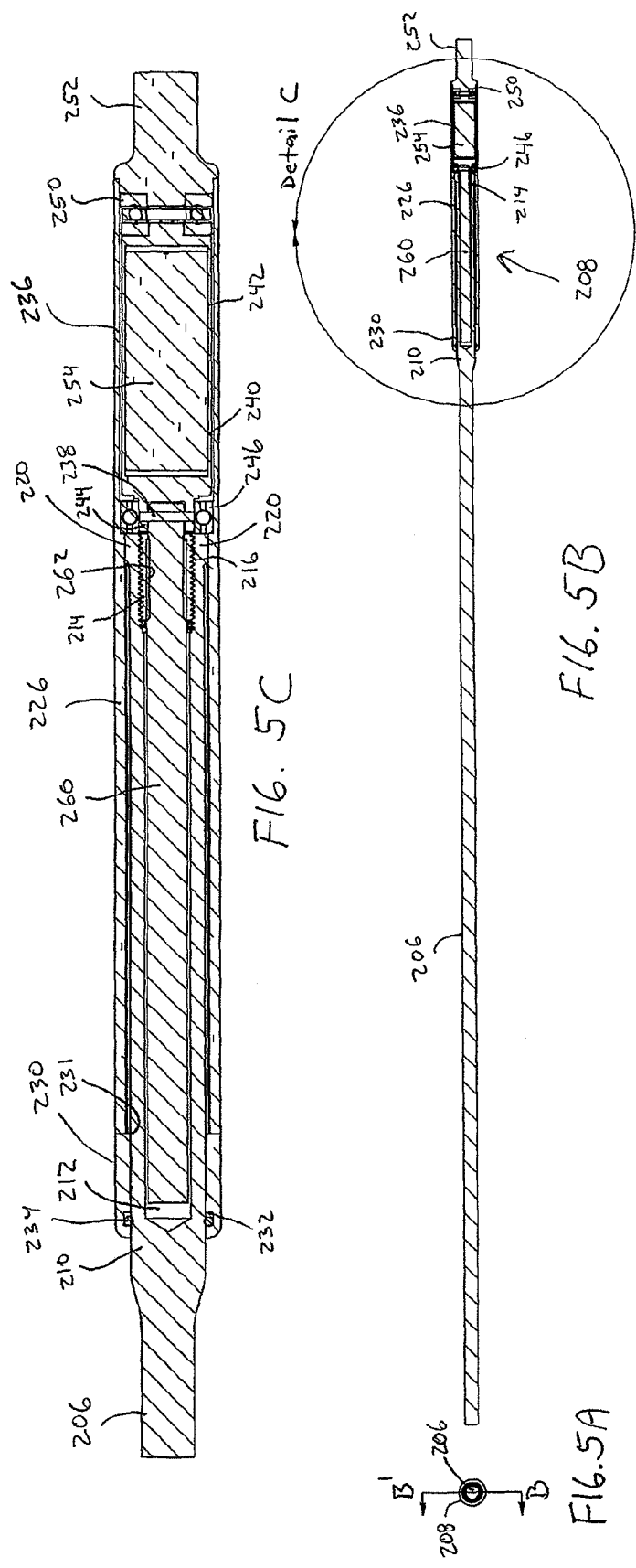

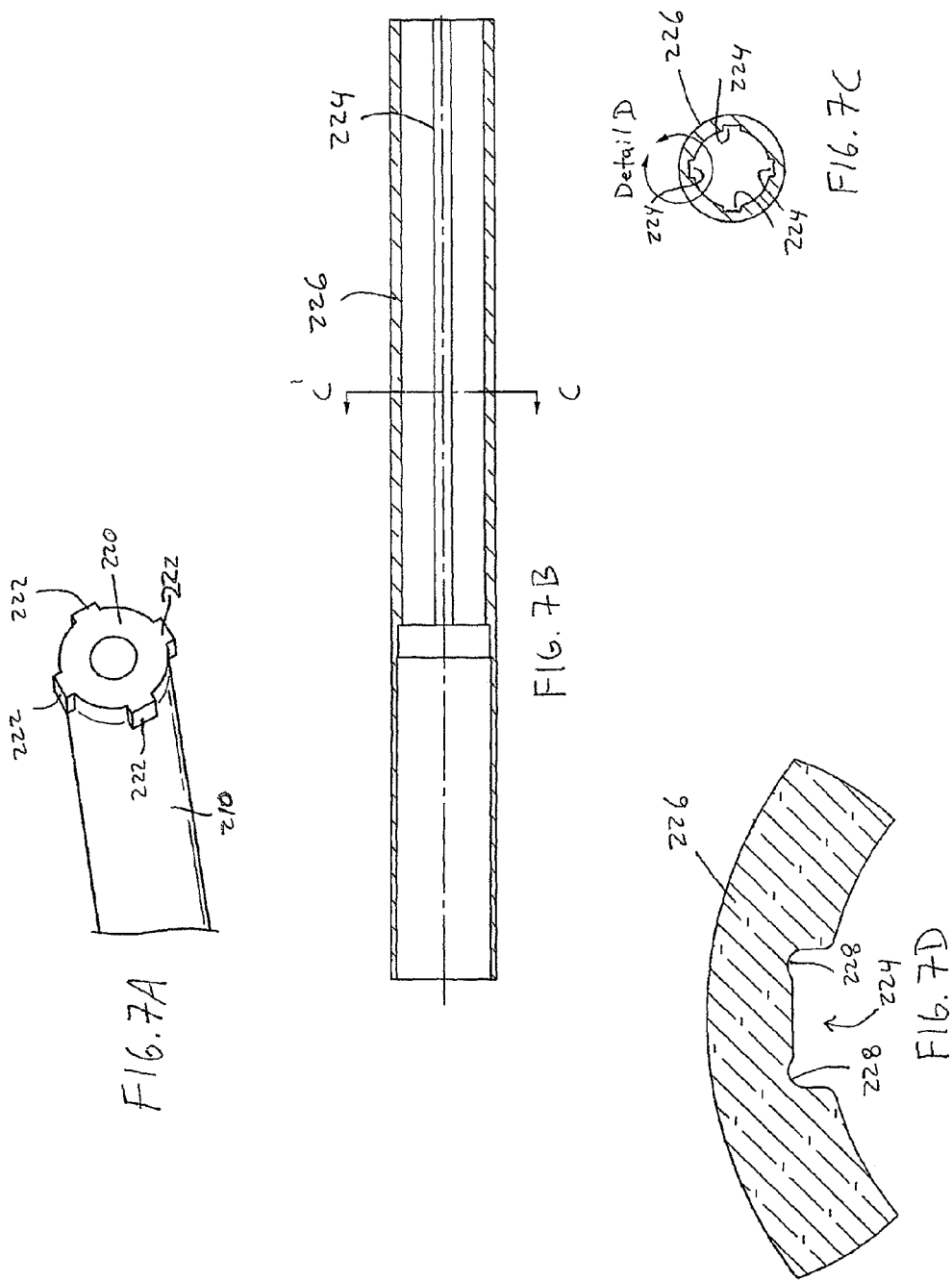

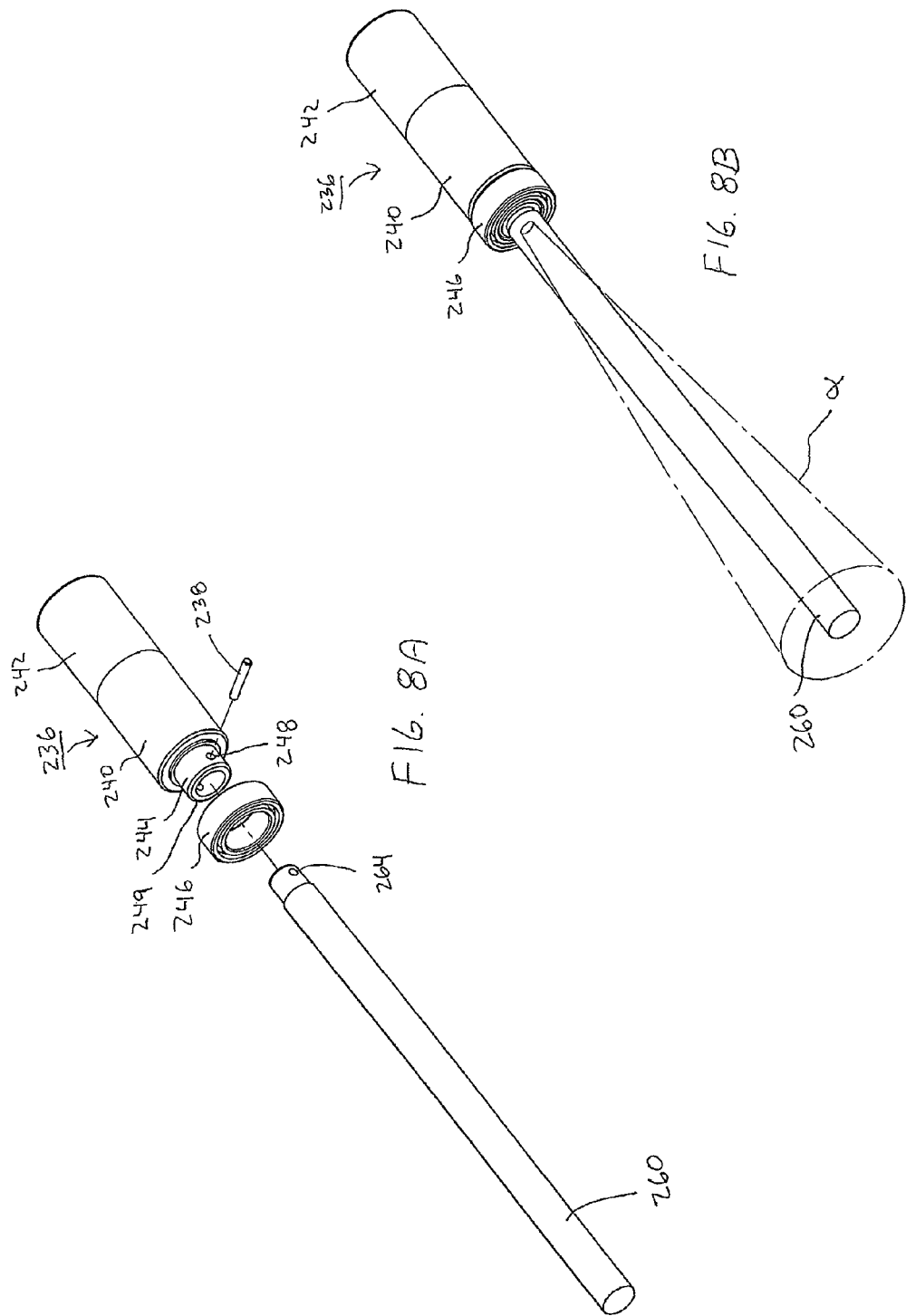

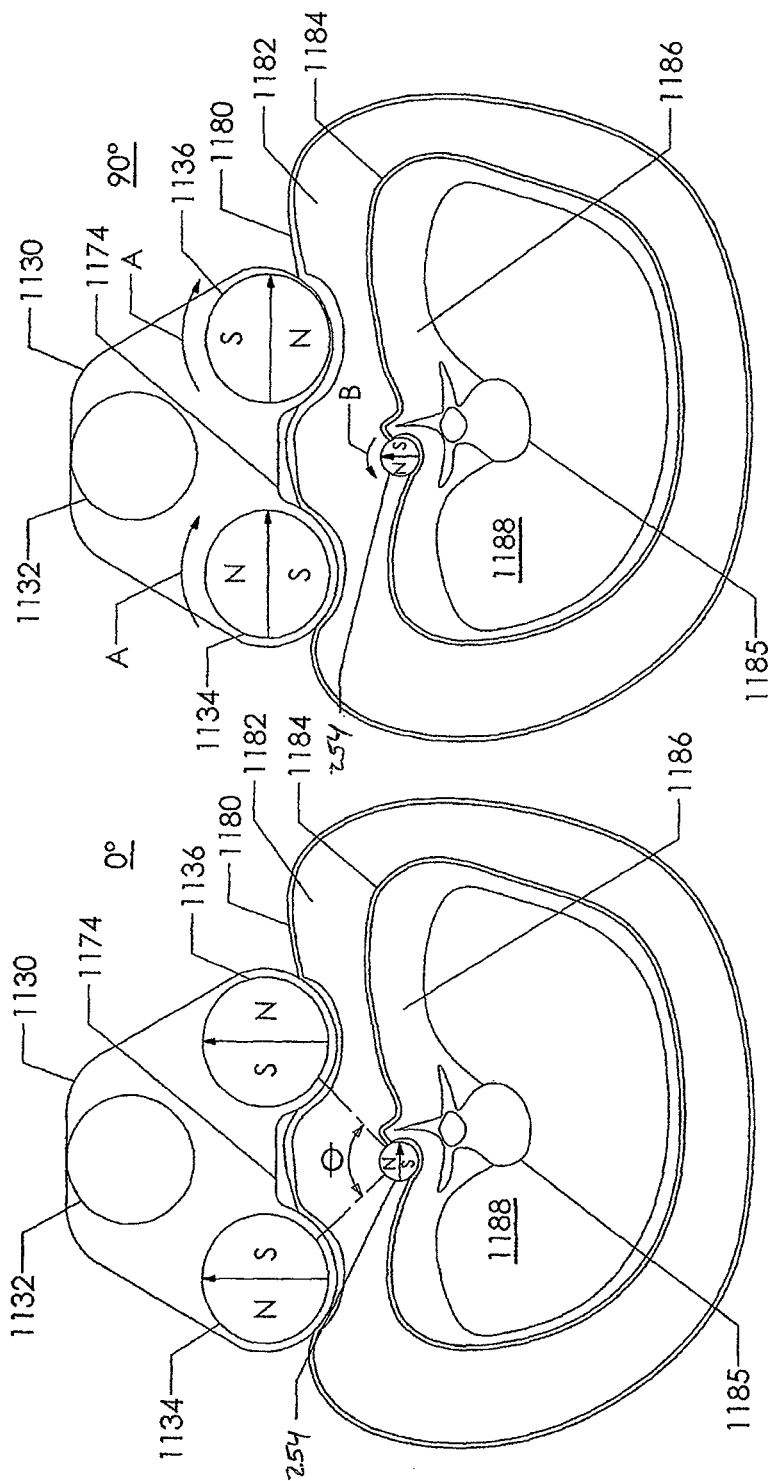

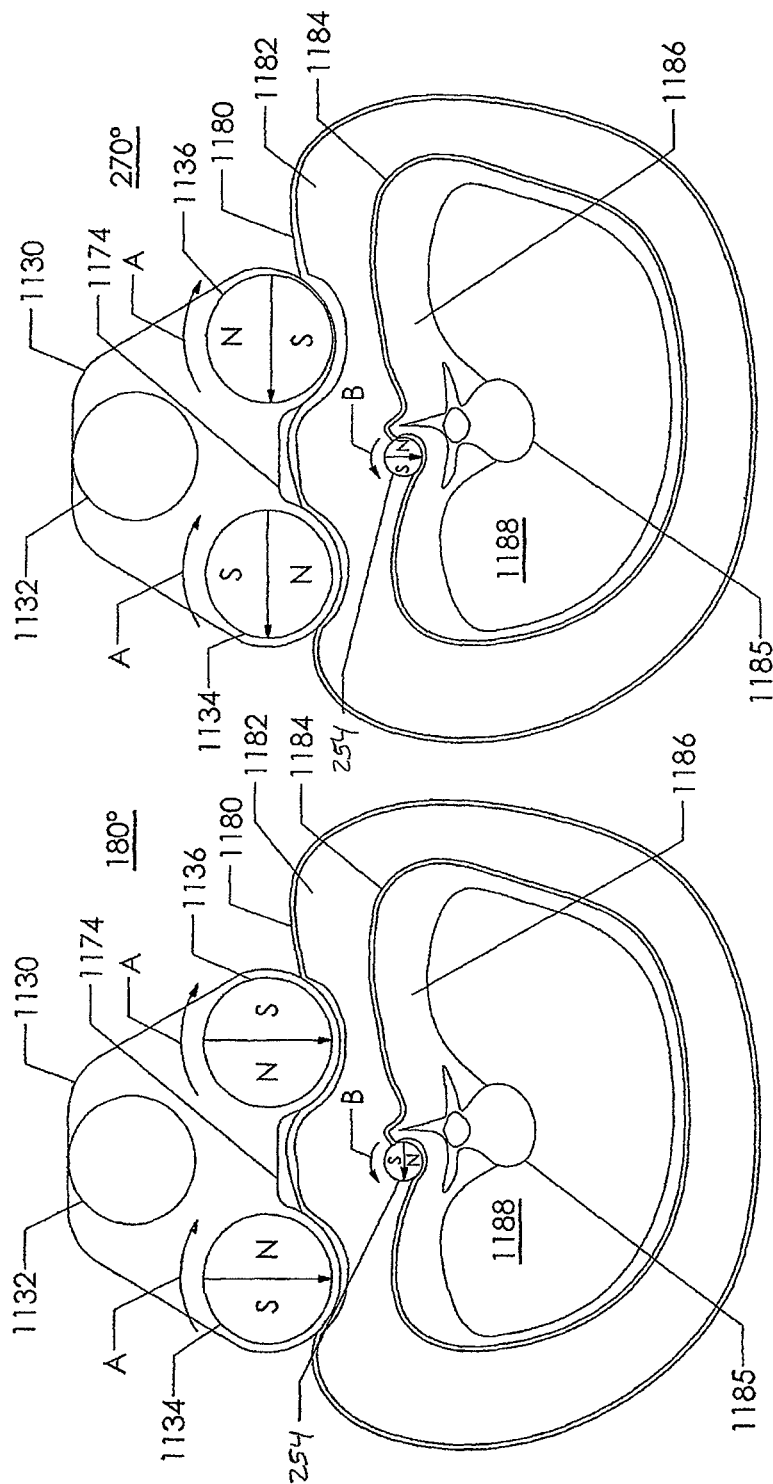

NON-INVASIVE ADJUSTABLE DISTRACTION SYSTEM

RELATED APPLICATION

This application is a continuation of U.S. patent application Ser. No. 12/391,109 filed on Feb. 23, 2009, now issued as U.S. Pat. No. 8,197,490, the entire disclosure of which is expressly incorporated by reference herein.

FIELD OF THE INVENTION

The field of the invention generally relates to medical devices for treating disorders of the skeletal system.

BACKGROUND OF THE INVENTION

Scoliosis is a general term for the sideways (lateral) curving of the spine, usually in the thoracic or thoracolumbar region. Scoliosis is commonly broken up into different treatment groups, Adolescent Idiopathic Scoliosis, Early Onset Scoliosis and Adult Scoliosis.

Adolescent Idiopathic Scoliosis (AIS) typically affects children between ages 10 and 16, and becomes most severe during growth spurts that occur as the body is developing. One to two percent of children between ages 10 and 16 have some amount of scoliosis. Of every 1000 children, two to five develop curves that are serious enough to require treatment. The degree of scoliosis is typically described by the Cobb angle, which is determined, usually from x-ray images, by taking the most tilted vertebrae above and below the apex of the curved portion and measuring the angle between intersecting lines drawn perpendicular to the top of the top vertebrae and the bottom of the bottom. The term idiopathic refers to the fact that the exact cause of this curvature is unknown. Some have speculated that scoliosis occurs when, during rapid growth phases, the ligamentum flavum of the spine is too tight and hinders symmetric growth of the spine. For example, as the anterior portion of the spine elongates faster than the posterior portion, the thoracic spine begins to straighten, until it curves laterally, often with an accompanying rotation. In more severe cases, this rotation actually creates a noticeable deformity, wherein one shoulder is lower than the other. Currently, many school districts perform external visual assessment of spines, for example in all fifth grade students. For those students in whom an "S" shape or "C" shape is identified, instead of an "I" shape, a recommendation is given to have the spine examined by a physician, and commonly followed-up with periodic spinal x-rays.

Typically, patients with a Cobb angle of 20° or less are not treated, but are continually followed up, often with subsequent x-rays. Patients with a Cobb angle of 40° or greater are usually recommended for fusion surgery. It should be noted that many patients do not receive this spinal assessment, for numerous reasons. Many school districts do not perform this assessment, and many children do not regularly visit a physician, so often, the curve progresses rapidly and severely. There is a large population of grown adults with untreated scoliosis, in extreme cases with a Cobb angle as high as or greater than 90°. Many of these adults, though, do not have pain associated with this deformity, and live relatively normal lives, though oftentimes with restricted mobility and motion. In AIS, the ratio of females to males for curves under 10° is about one to one, however, at angles above 30°, females outnumber males by as much as eight to one. Fusion surgery can be performed on the AIS patients or on adult scoliosis patients. In a typical posterior fusion surgery, an incision is made down the length of the back and Titanium or stainless steel straightening rods are placed along the curved portion. These rods are typically secured to the vertebral bodies, for example with hooks or bone screws, or more specifically pedicle screws, in a manner that allows the spine to be straightened. Usually, at the section desired for fusion, the intervertebral disks are removed and bone graft material is placed to create the fusion. If this is autologous material, the bone is harvested from a hip via a separate incision.

Alternatively, the fusion surgery may be performed anteriorly. A lateral and anterior incision is made for access. Usually, one of the lungs is deflated in order to allow access to the spine from this anterior approach. In a less-invasive version of the anterior procedure, instead of the single long incision, approximately five incisions, each about three to four cm long are made in several of the intercostal spaces (between the ribs) on one side of the patient. In one version of this minimally invasive surgery, tethers and bone screws are placed and are secured to the vertebra on the anterior convex portion of the curve. Currently, clinical trials are being performed which use staples in place of the tether/screw combination. One advantage of this surgery in comparison with the posterior approach is that the scars from the incisions are not as dramatic, though they are still located in a visible area, when a bathing suit, for example, is worn. The staples have had some difficulty in the clinical trials. The staples tend to pull out of the bone when a critical stress level is reached.

In some cases, after surgery, the patient will wear a protective brace for a few months as the fusing process occurs. Once the patient reaches spinal maturity, it is difficult to remove the rods and associated hardware in a subsequent surgery, because the fusion of the vertebra usually incorporates the rods themselves. Standard practice is to leave this implant in for life. With either of these two surgical methods, after fusion, the patient's spine is now straight, but depending on how many vertebra were fused, there are often limitations in the degree of flexibility, both in bending and twisting. As these fused patients mature, the fused section can impart large stresses on the adjacent non-fused vertebra, and often, other problems including pain can occur in these areas, sometimes necessitating further surgery. This tends to be in the lumbar portion of the spine that is prone to problems in aging patients. Many physicians are now interested in fusionless surgery for scoliosis, which may be able to eliminate some of the drawbacks of fusion.

One group of patients in which the spine is especially dynamic is the subset known as Early Onset Scoliosis (EOS), which typically occurs in children before the age of five, and more often in boys than in girls. This is a more rare condition, occurring in only about one or two out of 10,000 children, but can be severe, sometimes affecting the normal development of organs. Because of the fact that the spines of these children will still grow a large amount after treatment, non-fusion distraction devices known as growing rods and a device known as the VEPTR—Vertical Expandable Prosthetic Titanium Rib ("Titanium Rib") have been developed. These devices are typically adjusted approximately every six months, to match the child's growth, until the child is at least eight years old, sometimes until they are 15 years old. Each adjustment requires a surgical incision to access the adjustable portion of the device. Because the patients may receive the device at an age as early as six months old, this treatment requires a large number of surgeries. Because of the multiple surgeries, these patients have a rather high preponderance of infection.

Returning to the AIS patients, the treatment methodology for those with a Cobb angle between 20° and 40° is quite controversial. Many physicians proscribe a brace (for example, the Boston Brace), that the patient must wear on their body and under their clothes 18 to 23 hours a day until they become skeletally mature, for example to age 16. Because these patients are all passing through their socially demanding adolescent years, it is quite a serious prospect to be forced with the choice of either wearing a somewhat bulky brace that covers most of the upper body, having fusion surgery that may leave large scars and also limit motion, or doing nothing and running the risk of becoming disfigured and possibly disabled. It is commonly known that many patients have at times hidden their braces, for example, in a bush outside of school, in order to escape any related embarrassment. The patient compliance with brace wearing has been so problematic that there have been special braces constructed which sense the body of the patient, and keep track of the amount of time per day that the brace is worn. Patients have even been known to place objects into unworn braces of this type in order to fool the sensor. Coupled with the inconsistent patient compliance with brace usage, is a feeling by many physicians that braces, even if used properly, are not at all effective at curing scoliosis. These physicians may agree that bracing can possibly slow down or even temporarily stop curve (Cobb angle) progression, but they have noted that as soon as the treatment period ends and the brace is no longer worn, often the scoliosis rapidly progresses, to a Cobb angle even more severe than it was at the beginning of treatment. Some say the reason for the supposed ineffectiveness of the brace is that it works only on a portion of the torso, and not on the entire spine. Currently a prospective, randomized 500 patient clinical trial known as BrAIST (Bracing in Adolescent Idiopathic Scoliosis Trial) is enrolling patients, 50% of whom will be treated with the brace and 50% of who will simply be watched. The Cobb angle data will be measured continually up until skeletal maturity, or until a Cobb angle of 50° is reached, at which time the patient will likely undergo surgery.

Many physicians feel that the BrAIST trial will show that braces are completely ineffective. If this is the case, the quandary about what to do with AIS patients who have a Cobb angle of between 20° and 40° will only become more pronounced. It should be noted that the "20° to 40°" patient population is as much as ten times larger than the "40° and greater" patient population.

Currently, genetic scientists are at work to find one or more genes that may predispose scoliosis. Once identified, some are still skeptical as to whether gene therapy would be possible to prevent scoliosis, however the existence of a scoliosis gene would no doubt allow for easier and earlier identification of probable surgical patients.

SUMMARY OF THE INVENTION

In a first embodiment, a spinal distraction system includes a distraction rod having a first end and a second end, the first end being configured for affixation to a subject's spine at a first location, the distraction rod having a second end containing a recess having a threaded portion disposed therein. The distraction system further includes an adjustable portion configured for placement relative to the subject's spine at a second location remote from the first location, the adjustable portion comprising a housing containing a magnetic assembly, the magnetic assembly affixed at one end thereof to a lead screw via a locking pin passing transversely through the lead screw, the lead screw operatively coupled to the threaded portion.

In a second embodiment, a spinal distraction system includes a distraction rod having a first end and a second end, the first end being configured for affixation to a subject's spine at a first location, the distraction rod having a second end containing a recess having a threaded portion disposed therein. The adjustable portion is configured for placement relative to the subject's spine at a second location remote from the first location, the adjustable portion includes a housing containing a magnetic assembly, the magnetic assembly affixed at one end thereof to a lead screw, the lead screw operatively coupled to the threaded portion. The system further includes a recess disposed in an interior portion of the housing adjacent to one end, the recess having at least one o-ring therein dimensioned to form a fluid tight seal with the distraction rod.

BRIEF DESCRIPTION OF THE DRAWINGS

FIG. 5A is a cross-sectional view of a distraction rod and adjustable portion taken along a perpendicular axis to the longitudinal axis of the distraction rod.

FIG. 5B illustrates a cross-sectional view of the distraction rod and the adjustable portion taken along the line B'-B of FIG. 5A.

FIG. 5C illustrates an enlarged cross-sectional view of detail C of FIG. 5B.

FIG. 7A illustrates a perspective view of one end of a distraction rod illustrating the splined tip.

FIG. 7B is a side cross-sectional view of the tubular housing with the lead screw and magnetic assembly removed for clarity.

FIG. 7C is a cross-sectional view of the tubular housing taken along the line C'-C in FIG. 7B.

FIG. 7D illustrates a magnified view of detail D of FIG. 7C.

FIG. 8A is an exploded perspective view of the magnetic assembly, locking pin, bearing, and lead screw.

FIG. 8B is a perspective view illustrating the magnetic assembly coupled to the lead screw via the locking pin (hidden by the bearing). The off axis wiggle of the lead screw is illustrated by the cone-shaped envelope a.

FIG. 13A illustrates a cross-sectional representation of the external adjustment device being positioned on a patient's skin. FIG. 13A illustrates the permanent magnet in the 0° position.

FIG. 13B illustrates a cross-sectional representation of the external adjustment device being positioned on a patient's skin. FIG. 13B illustrates the permanent magnet in the 90° position.

FIG. 13C illustrates a cross-sectional representation of the external adjustment device being positioned on a patient's skin. FIG. 13C illustrates the permanent magnet in the 180° position.

FIG. 13D illustrates a cross-sectional representation of the external adjustment device being positioned on a patient's skin. FIG. 13D illustrates the permanent magnet in the 270° position.

DETAILED DESCRIPTION OF THE ILLUSTRATED EMBODIMENTS

Figure 1:
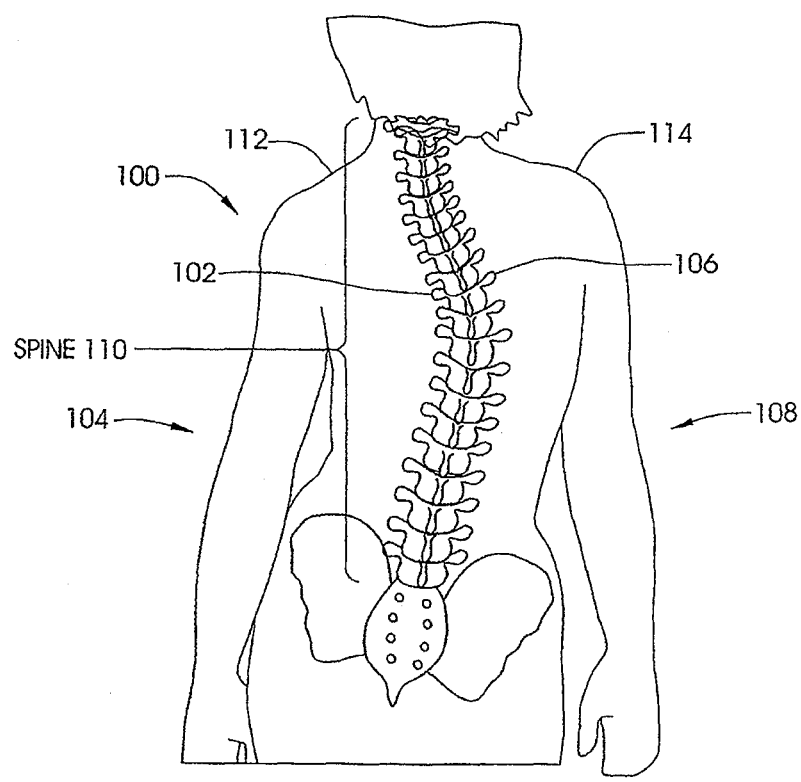
FIG. 1 illustrates the spine of a person with scoliosis.

FIG. 1 illustrates a patient 100 with scoliosis. The concave portion 102 of the spinal curve can be seen on the left side 104 of the patient 100, and the convex portion 106 can be seen on the right side 108 of the patient 100. Of course, in other patients, the concave portion 102 may appear on the right side 108 of the patient 100 while the convex portion 106 may be found on the left side 104 of the patient. In addition, as seen in FIG. 1, some rotation of the spine 110 is present, and unevenness between the left shoulder 112 and right shoulder 114 is seen.

Figure 2:
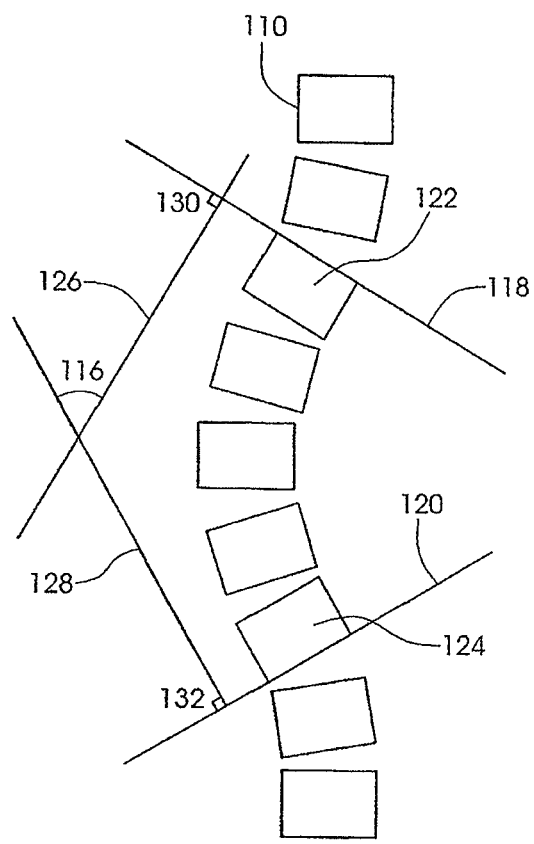
FIG. 2 illustrates the Cobb angle of a scoliotic spine.

FIG. 2 illustrates the Cobb angle 116 of a spine 110 of a patient with scoliosis. To determine the Cobb angle, lines 118 and 120 are drawn from vertebra 122 and 124, respectively. Intersecting perpendicular lines 126 and 128 are drawn by creating 90° angles 130 and 132 from lines 118 and 120. The angle 116 created from the crossing of the perpendicular lines 126 and 128 is defined as the Cobb angle. In a perfectly straight spine, this angle is 0°.

Figure 3:
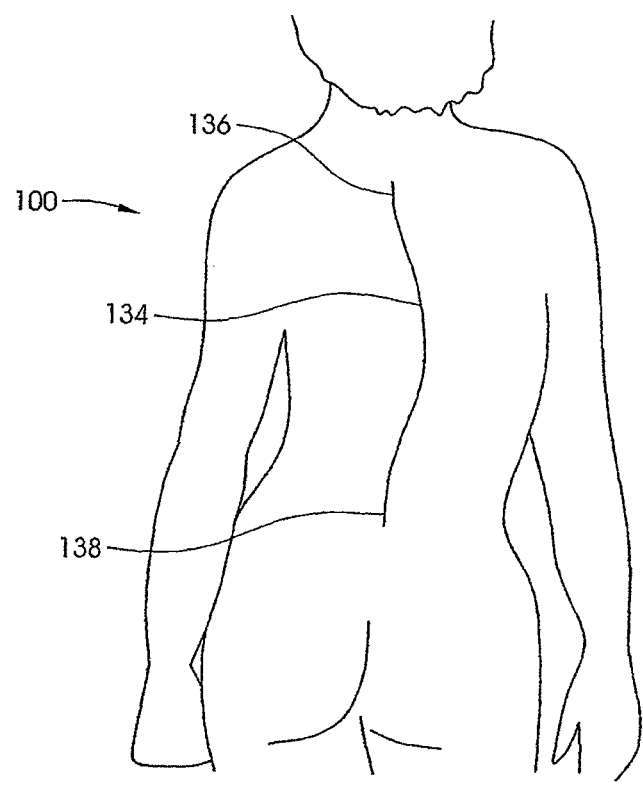
FIG. 3 illustrates the large incision made during prior art scoliosis fusion surgery.

In many Adolescent Idiopathic Scoliosis (AIS) patients with a Cobb angle of 40° or greater, spinal fusion surgery is typically the first option. FIG. 3 illustrates a long incision 134 formed in the patient 100 which is typically made during posterior scoliosis fusion surgery. This type of fusion surgery is known in the prior art. The long incision 134 extends between an upper end 136 and a lower end 138. The length of this incision 134 is longer than the length of the section of the vertebra to be fused. The actual length between the upper end 136 and the lower end 138 varies, depending on the size of the patient, and the extent of the scoliosis, but in AIS patients this length is significantly longer than 15 cm. More typically, it is longer than 25 cm.

Figure 4:
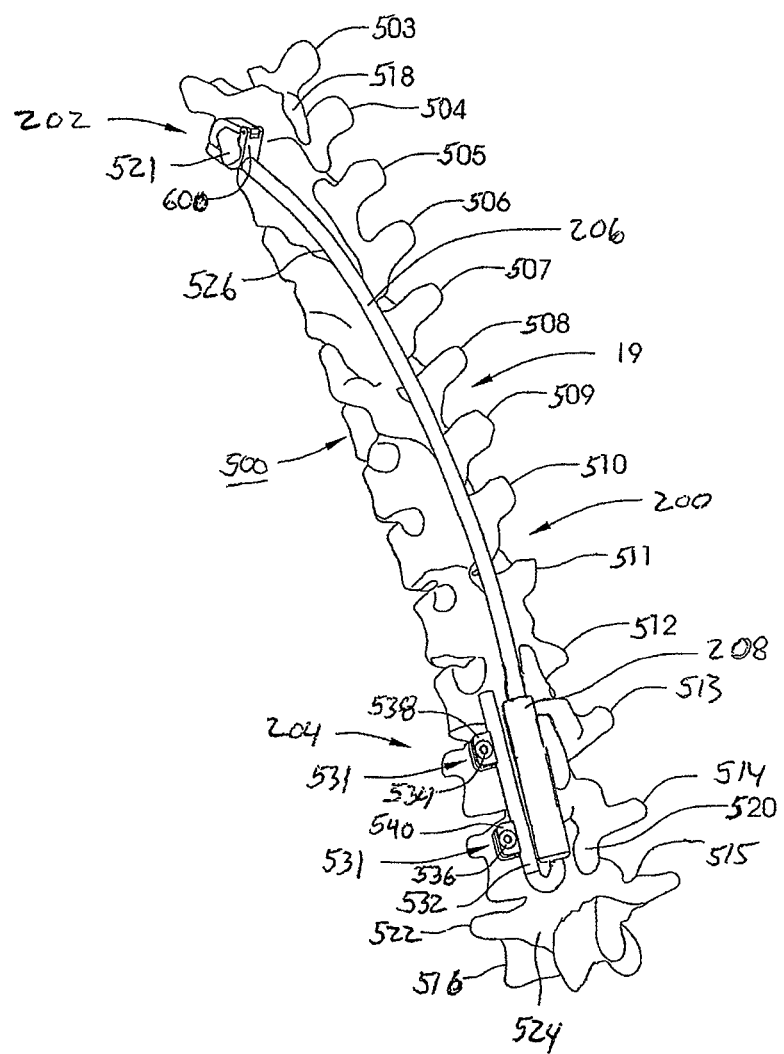
FIG. 4 illustrates an exemplary distraction device mounted on the spine of a subject.

FIG. 4 illustrates a distraction device 200 for treating scoliosis according to one embodiment of the invention. The distraction device 200, which is an implantable device, is fixated at its upper end 202 and lower end 204 to the patient's spine 500. The illustrated example of the spine 500 includes the particular thoracic and lumbar vertebrae that typically encompass a scoliotic curve, for example the curve of a patient with adolescent idiopathic scoliosis. The T3 through T12 thoracic vertebrae, 503, 504, 505, 506, 507, 508, 509, 510, 511, 512, respectively and the L1 through L3 vertebrae, 513, 514, 515 are depicted in FIG. 4, not in a severe scoliotic condition, but in a very slight residual curve that represents a modest curve that has been partially or completely straightened during the implantation procedure.

Each vertebra is different from the other vertebra by its size and shape, with the upper vertebra generally being smaller than the lower vertebra. However, generally, the vertebrae have a similar structure and include a vertebral body 516, a spinous process 518, 520, laminae 526, transverse processes 521, 522 and pedicles 524. In this embodiment, the distraction device 200 includes a distraction rod 206 which is adjustable (lengthwise) via a coupled adjustable portion 208. The distraction device 200 is fixated to the spine 500 via a clamp 600 at the upper end 202 of the distraction rod 206. In FIG. 4, the clamp 600 is secured around the transverse process 521 of the T4 vertebra 504. Alternatively, the clamp 600 may be secured around an adjacent rib (not shown) or rib facet. In still another alternative, the clamp may be replaced by a laminar and pedicle hook system, or pedicle screw system. Exemplary pedicle hook systems or pedicle screw systems may be found in U.S. patent application Ser. Nos. 12/121,355 and 12/250,442 which are incorporated by reference as if set forth fully herein.

Referring back to FIG. 4, the distraction device 200 is illustrated as being fixated to the spine 500 with a pedicle screw system 531 comprising a connecting rod 532 and two toe clamps 538, 540. The connecting rod 532 is shown curving back on itself in the shape of a "J." The connecting rod 532 then interfaces with the adjustable portion 208. As explained in more detail below. The adjustable portion 208 preferably contains a magnetic assembly having a permanent magnet configured to drive a lead screw that, depending on the direction of rotation of the internal magnet, will extend or retract the distraction rod 206 using the adjustable portion 208. Lengthening of the distraction rod 206, for example, will impart a distraction force to the spine 500. Retracting the distraction rod 206 will lower or remove the distraction force on the spine 500, for example if too high a distraction force causes pain or complications.

Still referring to FIG. 4, a locking screw 534 can be loosened to adjust the angle of the connecting rod 532 into the desired orientation and then locking screw 534 can be tightened so that toe clamp 538 securely holds connecting rod 532 in place without further rotation. The second toe clamp 540 is adjusted in the same way, by tightening locking screw 536. Because a scoliotic spine is also rotated (usually the center section is rotated to the right in AIS patients), the non-fusion embodiment presented here allows de-rotation of the spine 500 to happen naturally, because there is no fixation at the middle portion of the distraction device 200.

In order to further facilitate this de-rotation, the distraction device 200 may allow for free rotation at its ends. For example, the adjustable portion 208 may be coupled to the connecting rod 532 via an articulating joint. U.S. patent application Ser. Nos. 12/121,355 and 12/250,442 describe various articulating interfaces and joints that may be utilized to couple the adjustable portion 108 to the connecting rod 532 or the like.

It should be noted that distraction rod 206 may be pre-curved with the typical shape of a normal saggital spine, but it should also be noted that the curve may be slightly different than standard scoliosis fusion instrumentation, because in the non-fusion embodiment described herein, the distraction device 200 is not flush with the spine but rather is placed either subcutaneous or sub-fascial, and thus is not below the back muscles. The only portions of the distraction device 200 that are designed to be placed below the muscles are the clamp 600 and the portion of the distraction rod 206 immediately adjacent the clamp 600, the pedicle screw system 531 and the connecting rod 532. Thus, FIG. 4 illustrates an embodiment in which the bulk of the hardware associated with the distraction device 200 is placed over the muscle. It should be understood, however, that in alternative configurations, any other part of the entire implantable embodiment may be placed under the muscle (i.e., sub-muscular). It should be appreciated that a much smaller amount of muscle needs to be dissected during the procedure in comparison with current fusion procedures. This will allow for a much shorter procedure, much less blood loss, much quicker recovery, and less time in the hospital/less risk of infection. Further, it may be desirable to produce the "J" curve of the connecting rod 532 or any other curve at the connecting rod 532 with optional flanges or ribs at their highest stress points in order to increase their durability in demanding implant conditions.

FIGS. 5A-5C illustrate cross-sectional views of the interface of the distraction rod 206 with the adjustable portion 208. FIG. 5A is a cross-sectional view of the distraction rod 206 and adjustable portion 208 taken along a perpendicular axis to the longitudinal axis of the distraction rod 206. FIG. 5B illustrates a cross-sectional view of the distraction rod 206 and the adjustable portion 208 taken along the line B'-B of FIG. 5A. FIG. 5C illustrates an enlarged cross-sectional view of detail C of FIG. 5B. As best seen in FIG. 5C, an end 210 of the distraction rod 206 includes an elongate recess 212. The elongate recess 212 may have a length of around 60 mm. The recess 212 is dimensioned to receive a lead screw 260. The lead screw 260 may be made from a high strength material such as, for example, titanium. At least a portion of the lead screw 260 includes external threads 262 that are configured to engage with a nut 214 integrated into the recess 212. The nut 214 provides a threaded portion on the recess 212 of the distraction rod 206. The lead screw 260 may have, for example, 80 threads per inch although more or less could be used. The nut 214 may includes threads or a chamfered surface 216 on the outer diameter in order to better ensure a secure attachment to the inner diameter of the recess 212 of the distraction rod 206. For example, the nut 214 may be bonded to the distraction rod 206 using an adhesive such as EPOTEK 353ND, available from EPDXY TECHNOLOGY, INC., 14 Fortune Drive, Billerica, Mass. This allows the distraction rod 206 to be fabricated from a single piece of stronger material. It also provides for clearance between the lead screw 260 and internal diameter of the distraction rod 206. Alternatively, a threaded portion may be directly formed in the recess 212 without the aid of a separate nut 214.

Figure 6A:
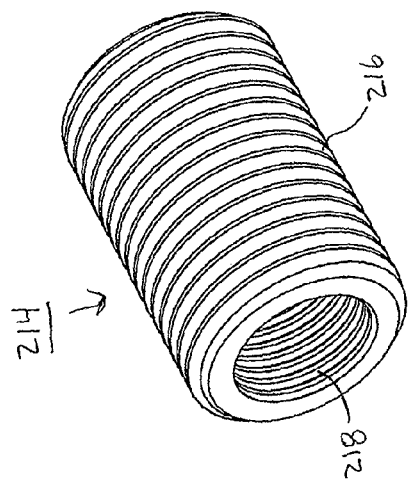
FIG. 6A illustrates a perspective view of a nut disposed within an interior recess located at one end of the distraction rod.
Figure 6C:
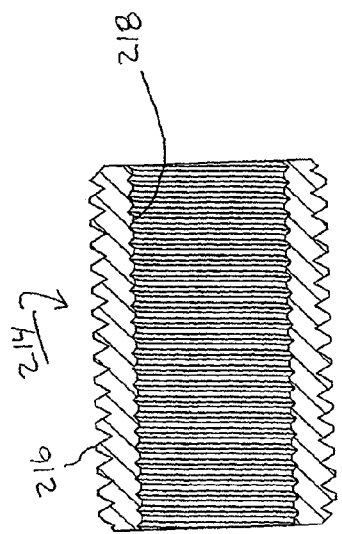
FIG. 6C is a cross-sectional view of the nut taken along the line C'-C of FIG. 6B.
Figure 6B:
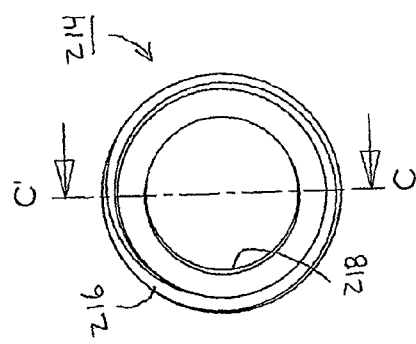
FIG. 6B is an end view of the nut of FIG. 6A.

FIGS. 6A-6C illustrate separate views of the nut 214. The nut includes internal threads 218 that engage with the outer threads 262 of the lead screw 260. In one aspect, the nut 214 is made from aluminum-bronze #630. By using dissimilar metals (titanium for lead screw 260 and aluminum-bronze for the nut 214) with different hardness values results in less gall/bind between the lead screw 260 and the nut 214. This further enables to the lead screw 260 and the nut 214 to operate with reduced friction. Optionally, various wet or dry lubricants may be used to reduce friction between the lead screw 260 and the nut 214. One example of a wet lubricant includes biocompatible silicone oil such as MED-360 (100,000 cp) available from NuSil Technology, 1050 Cindy Lane, Carpinteria, Calif. 93013.

Referring back to FIG. 5C, the end of the distraction rod 206 includes a splined tip 220 that includes one or more protrusions 222 that interface with corresponding longitudinal grooves 224 (not shown in FIG. 5C) disposed within an inner surface of a tubular housing 226. FIG. 7A illustrates a perspective view of the splined tip 220. The splined tip 220 is illustrated with four (4) protrusions 222 that interface with four (4) corresponding longitudinal grooves 224 (two pairs in symmetric opposition) formed inside a tubular housing 226 (illustrated in FIGS. 7B-D). The longitudinal grooves 224 may be formed by wire EDM machining. While FIGS. 7A-7D illustrate an embodiment that uses four (4) protrusions 222 along with four (4) longitudinal grooves 224 there may be more or less. The tight tolerance of the splined tip 220 with the longitudinal grooves 224 keeps the distraction rod 206 centered within the tubular housing 226. In addition, the combination of the splined tip 220 and corresponding grooves 224 act as an anti-rotation feature that prevents the distraction rod 206 from rotating relative to the tubular housing 226. This may be necessary to allow the distraction device 200 to be "rigidized" in the event the device is used in fusion applications, instead of the non-fusion applications described. For example, in a fusion application, it is desired that the spine 500 not be able to flex or rotate much during the months that the fusion is taking place. In either the fusion applications or the non-fusion applications, the anti-rotation features prevent inadvertent extension and/or retraction of the distraction rod 206 resulting from, for instance, patient movements.

FIG. 7C is a cross-sectional view of the tubular housing 226 taken along the line C'-C in FIG. 7B. FIG. 7D illustrates a magnified view of detail D of FIG. 7C. In this illustrated embodiment, as best seen in the detailed view of FIG. 7D, small reliefs 228 are incorporated into the sides or corners of the longitudinal grooves 224. These reliefs 228 may be slight over cut wire EDM notches that prevent the corners of the protrusions 222 from contacting the inner wall of the tubular housing 226. Less contact between the protrusions 222 and the longitudinal grooves 224 results in less frictional forces and reduces the likelihood of binding. Optionally, the tops of the protrusions 222 could be curved, for example, cut from a diameter instead of a square. This rounding of the protrusions 222 would keep the protrusions 222 from binding with the longitudinal grooves 224 when torsional stresses are imparted between the distraction rod 206 and the adjustable portion 208. This optional modification makes the distraction rod 106 easier to manufacture and eliminates the need for the relief 228 overcuts.

Referring back to FIGS. 5B and 5C, an o-ring gland 230 is affixed or otherwise bonded to an end of the tubular housing 226. The o-ring gland 230 is, for example, electron beam (e-beam) or laser welded to the end of the tubular housing 226. As best illustrated in FIG. 5C, the o-ring gland 230 has an inner diameter than is less than inner diameter of the tubular housing. In this regard, a stop 231 is created that prevents further advancement of the splined tip 220 from exiting the tubular housing 226. This will assure that the distraction rod 206 cannot be over-distracted in relation to the adjustable portion 208, and thus that integrity is maintained (e.g., the distraction rod 206 does not disconnect or jam). The o-ring gland 230 further includes a recess 232 that is dimensioned to receive an o-ring 234. The o-ring 234 may be formed from a biocompatible material such as 70 durometer ethylene propylene diene M-class rubber (EPDM) available from Precision Associates, Inc., 740 North Washington Ave., Minneapolis, Minn., 55401-1188. The o-ring 234 may have an inner diameter of around 0.241 inches +/−0.005 inches with a cross-section of 0.030 inches +/−0.003 inches. The outer diameter of the end 210 of the distraction rod 206 may be around 0.25 inches. A biocompatible lubricant such as biocompatible silicone oil (e.g., MED-360 available from NuSil Technology) may be applied to the o-ring 234. The o-ring 234 thus forms a fluid-tight seal with the outer surface of the distraction rod 206.

Thus, the distraction rod 206 is able to telescope relative to the housing 226 while simultaneously preventing foreign matter from entering the housing 226. While a single o-ring 234 is illustrated in FIG. 5C, multiple o-rings may also be used to provide additional confidence in seal integrity. With respect to the single o-ring 234 illustrated in FIG. 5C, the radial compression of the o-ring is greater than 7%, and preferably falls within the range between about 13% to 18%. Further, the fill volume of the recess 232 of the o-ring gland 230 is designed to be less than 75% in all cases and more particularly, within a range of about 40% to about 54%. It is desired to have all surfaces that contact the o-ring 234 be smooth. For example, the recess 232 may be designed with a smooth surface finish. Rough finishes can damage the o-ring 234 or provide a potential leakage path across sealing surfaces. An exemplary surface finish is 16 microinches RMS.

The o-ring 234 may provide several advantages in keeping foreign materials out of the tubular housing 226. In particular, positive air pressure within the tubular housing 226 may be created during the manufacturing process. The positive air pressure provides additional stored pushing force to aid in distraction of the distraction rod 206. The positive air pressure also aids in preventing ingress of foreign matter. The use of the o-ring 234 within the recess 232 of the o-ring gland 230 permits telescopic movement of the distraction rod 206 while at the same time seals in the interior of the tubular housing 226 from the exterior environment. In vivo animal testing has confirmed that such an arrangement has maintained the integrity of the tubular housing 226 for over seven months. In a seven month study conducted in vivo in pigs, the distraction device 200 was removed and the adjustable portion 208 was fully functional.

As best seen in FIGS. 5C, 8A, 8B, the distraction rod 206 is coupled to a magnetic assembly 236 via a locking pin 238. The lead screw 260 contains an aperture 264 transversely oriented with respect to the longitudinal axis of the lead screw 260 at the proximal end that is dimensioned to receive the locking pin 238. The magnetic assembly 236, which is described in more detail below, includes an upper cup 240 and a lower cup 242. The upper cup 240 terminates at a receptacle 244 that has an inner diameter dimensioned to receive the end of the lead screw 260 containing the aperture 264. The receptacle 244 also has an outer diameter that interfaces with an interior surface a bearing 246. The bearing 246 may include a radial ball bearing that rotatably holds the upper cup 240 (via the receptacle 244) within the tubular housing 226. The receptacle 244 includes apertures 248, 249 through which the locking pin 238 is placed to lock the lead screw 260 to the magnetic assembly 236. The locking pin 238 remains in place because, when in place, the bearing 246 prevents the locking pin 238 from sliding out of the apertures 248, 249 in the receptacle 244. This overlap also advantageously shortens the overall length of the magnetic assembly 236. Alternatively, only a single aperture 248 may be used and the opposing end of the locking pin 238 may interface with a recess located on the opposing side of the receptacle 244.

The interface between the lead screw 260 and the magnetic assembly 236 has several functions. The interface must withstand heavy compressive loads. It also may need to withstand large tensile loads. Furthermore, the interface must transmit torque from the rotating magnetic assembly 236 to the lead screw 260. The interface must also maintain the concentric alignment between the lead screw 260 and the nut 214. With respect to compressive loads, these are transmitted down the lead screw 260 and across the locking pin 238 and into the magnetic assembly 236. The magnetic assembly 236, as best seen in FIG. 5C, rides on a thrust ball bearing 250. An end cap 252 located at one end of the tubular housing 226 is provided. The end cap 252 may be laser or e-beam welded to the tubular housing 226. The end cap 252 may be used to couple or otherwise interface with a joint (e.g., articulating joint) that is coupled or otherwise connected to, for example, a connecting rod 532 such as that illustrated in FIG. 4.

With respect to tensile loads, these are transmitted from the magnetic assembly 236 across the locking pin 238 and up the lead screw 260. The locking pin 238 pulls on the magnetic assembly which is retained by the bearing 246. The locking pin 238 may be made from a strong material such as, for instance, 440C stainless steel that has been heat treated for added strength. For instance, the 440C stainless steel may be heated to achieve a hardness of at least C58 Rockwell. The locking pin 238 may have a length of around 0.185 inches and a diameter of around 0.0314 inches. The ends of the locking pin 238 may be beveled. The ultimate pull strength at which the locking pin 238 fails has been determined in testing to be 353 lbs. Thus, the locking pin 238 retains its structural integrity up to a tensile load force of about 350 lbs. This is significantly higher than the highest expected distraction force. For example, other researchers have found that peak distraction forces experienced by growing rods are at or less than 124 lbs. See Teli et al., *Measurement of Forces Generated During Distraction of Growing Rods, J. Child Orthop* 1:257-258 (2007). The locking pin 238 described herein thus provides a wide margin of safety given the anticipated distraction forces that are experienced by the distraction rod 206.

Torquing forces are transmitted from the magnetic assembly 236 to the lead screw 260 via the locking pin 238. Because the torque available is limited, even small mechanical losses due to component binding is a problem. Here, however, the clearances between the locking pin 238 and the lead screw 260 allow the lead screw 260 to "wiggle" freely in the upper cup 240 of the magnetic assembly 236. FIG. 8B illustrates the cone-shaped envelope a traced by the off axis "wiggle" permitted by the interface of the locking pin 238 with the lead screw 260. This wiggle or play allows the lead screw 260 and nut 214 to self-align to reduce binding.

Figure 9B:
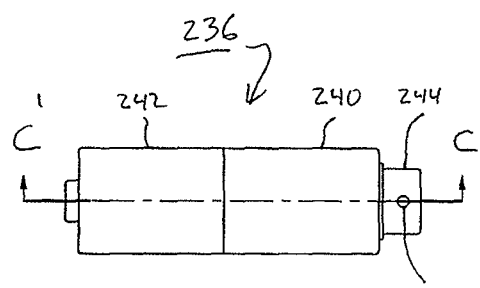
FIG. 9B is a side view of the magnetic assembly.
Figure 9A:
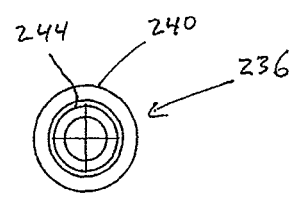
FIG. 9A is an end view of the magnetic assembly.
Figure 9C:
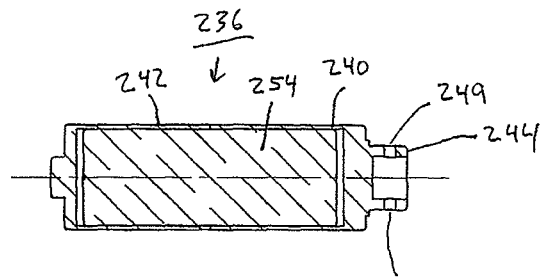
FIG. 9C is a cross-sectional view of the magnetic assembly illustrated in FIG. 9B taken along the line C'-C.

FIGS. 9A-9C illustrate the magnetic assembly 236. FIG. 9A illustrates an end view of the magnetic assembly 236 while FIG. 9B illustrates a side view of the magnetic assembly 236. FIG. 9C is a cross-sectional view of the magnetic assembly 236 taken along the line C'-C of FIG. 9B. The magnetic assembly 236, as explained above, includes an upper cup 240 and a lower cup 242. A permanent magnet 254 is located in the recess formed between the interior portions of the upper cup 240 and the lower cup 242. The permanent magnet 254 is preferably a cylindrical magnet having a diameter of about 0.28 inches and a length of about 0.73 inches although other dimensions may be used. The permanent magnet 254 may include, for example, a rare earth magnet formed from, for instance, Neodynium-Iron-Boron. The magnet may be made from a grade of N35 or higher, for example a grade of N50. The permanent magnet 254 is bonded or otherwise affixed to the upper cup 240 and the lower cup 242. An epoxy adhesive such as EPOTEK 353ND may be used to bond the permanent magnet 254 to the upper cup 240 and the lower cup 242. This allows torque applied to the permanent magnet 254 to be transferred to the upper cup 240 and thus the lead screw 260. The permanent magnet 254 is shorter in length than the combined lengths of the internal cavities of the upper cup 240 and lower cup 242. This assures that when the magnetic assembly 236 is under compression, the upper cup 240 and the lower cup 242 are stressed instead of the permanent magnet 254.

Figure 10:
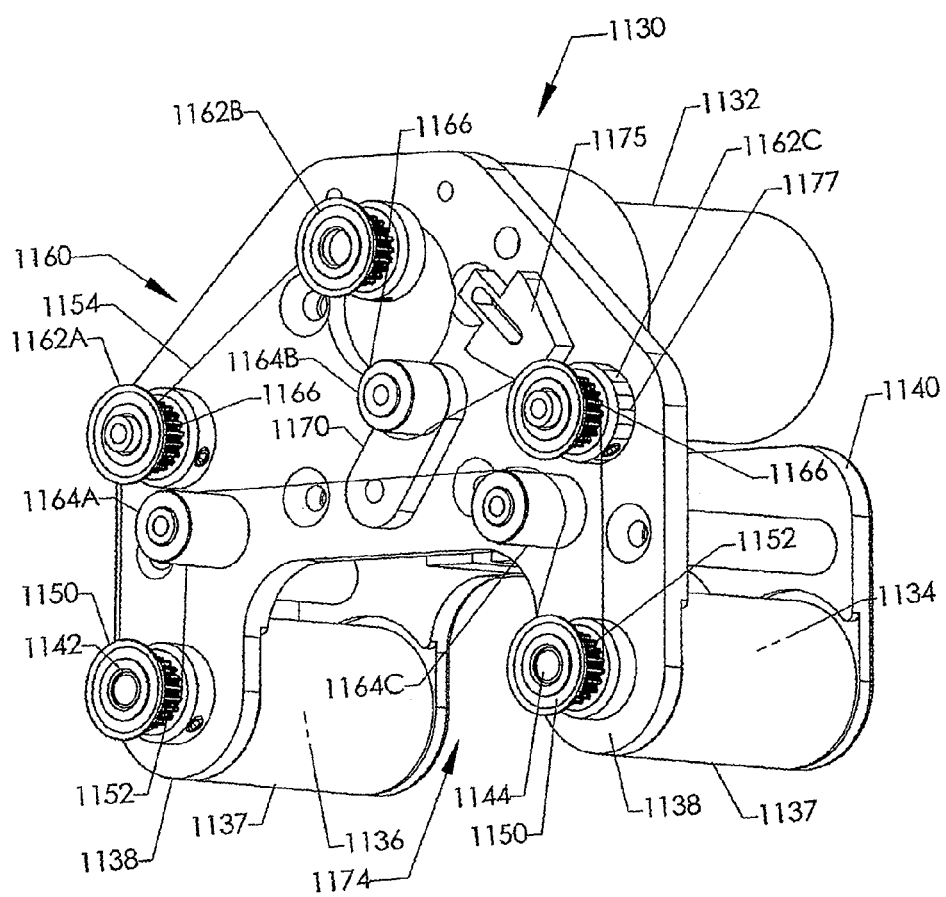
FIG. 10 illustrates a perspective view of an external adjustment device according to one embodiment. The outer housing or cover is removed to illustrate the various aspects of the external adjustment device.

FIG. 10 illustrates an external adjustment device 1130 that may be used to externally impart rotational motion or "drive" the magnetic assembly 236 located within the distraction device 200. The external adjustment device 1130 includes a motor 1132 that is used to impart rotational movement to two permanent magnets 1134, 1136. The two permanent magnets 1134, 1136 are located in the same driver 1130 and are configured for placement on the same side of the body of the patient or subject. The motor 1132 may include, for example, a DC powered motor or servo that is powered via one or more batteries (not shown) integrally contained within the external adjustment device 1130. Alternatively, the motor 1132 may be powered via a power cord or the like to an external power source. For example, the external power source may include one or more batteries or even an alternating current source that is converted to DC.

Still referring to FIG. 10, the two permanent magnets 1134, 1136 are preferably cylindrically-shaped permanent magnets. The permanent magnets may be made from, for example, a rare earth magnet material such as Neodymium-Iron-Boron (NdFeB) although other rare earth magnets are also possible. For example, each magnet 1134, 1136 may have a length of around 1.5 inches and a diameter of around 1.0 to 3.5 inches. Both magnets 1134, 1136 are diametrically magnetized (poles are perpendicular the longitudinal axis of each permanent magnet 1134, 1136). The magnets 1134, 1136 may be contained within a non-magnetic cover or housing 1137. In this regard, the magnets 1134, 1136 are able to rotate within the stationary housing 1137 that separates the magnets 1134, 1136 from the external environment. Preferably, the housing 1137 is rigid and relatively thin walled at least at the portion directly covering the permanent magnets 1134, 1136, in order to minimize the gap between the permanent magnets 1134, 1136 and the magnetic assembly 236 (as shown in FIGS. 13A-13D).

As seen in FIG. 10, the permanent magnets 1134, 1136 are rotationally mounted between opposing bases members 1138, 1140. Each magnet 1134, 1136 may include axles or spindles 1142, 1144 mounted on opposing axial faces of each magnet 1134, 1136. The axles 1142, 1144 may be mounted in respective bearings (not shown) that are mounted in the base members 1138, 1140. As seen in FIG. 10, driven pulleys 1150 are mounted on one set of axles 1142 and 1144. The driven pulleys 1150 may optionally include grooves or teeth 1152 that are used to engage with corresponding grooves or teeth 1156 (partially illustrated in FIG. 11) contained within a drive belt (indicated by path 1154).

Figure 12:
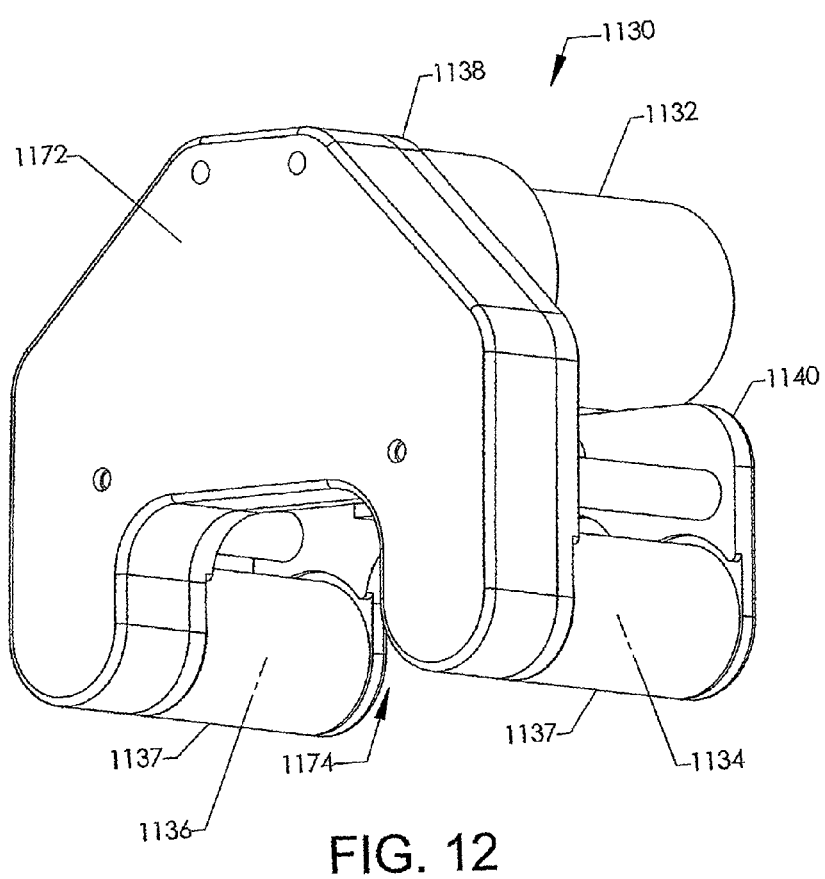
FIG. 12 illustrates a perspective view of an external adjustment device of FIG. 10 with the outer housing or cover in place.

Still referring to FIG. 10, the external adjustment device 1130 includes a drive transmission 1160 that includes the two driven pulleys 1150 along with a plurality of pulleys 1162A, 1162B, 1162C and rollers 1164A, 1164B, 1164C on which the drive belt 1154 is mounted. The pulleys 1162A, 1162B, 1162C may optionally include grooves or teeth 1166 used for gripping corresponding grooves or teeth 1156 of the drive belt 1154. Pulleys 1162A, 1162B, 1162C and rollers 1164A, 1164B, 1164C may be mounted on respective bearings (not shown). As seen in FIG. 10, pulley 1162B is mechanically coupled to the drive shaft (not shown) of the motor 1132. The pulley 1162B may be mounted directly to the drive shaft or, alternatively, may be coupled through appropriate gearing. One roller 1164B is mounted on a biased arm 1170 and thus provides tension to the belt 1154. The various pulleys 1150, 1162A, 1162B, 1162C and rollers 1164A, 1164B, 1164C along with the drive belt 1154 may be contained within a cover or housing 1172 that is mounted to the base 1138 (as seen in FIG. 12). For safety and convenience, it may be desired for the external adjustment device 1130 to have a removable safety cover that would be placed over the portion containing the permanent magnets 1134, 1136, for example during storage, so that the high magnetic field cannot come closely in contact with anything that would be strongly attracted to it or damaged by it. The external adjustment device 1130 may also be supplied in a case, for example, a case that has a sheet made of a magnetic shielding material, to minimize the magnetic field external to the case. Giron or mu-metal are two examples of this material.

Figure 11:
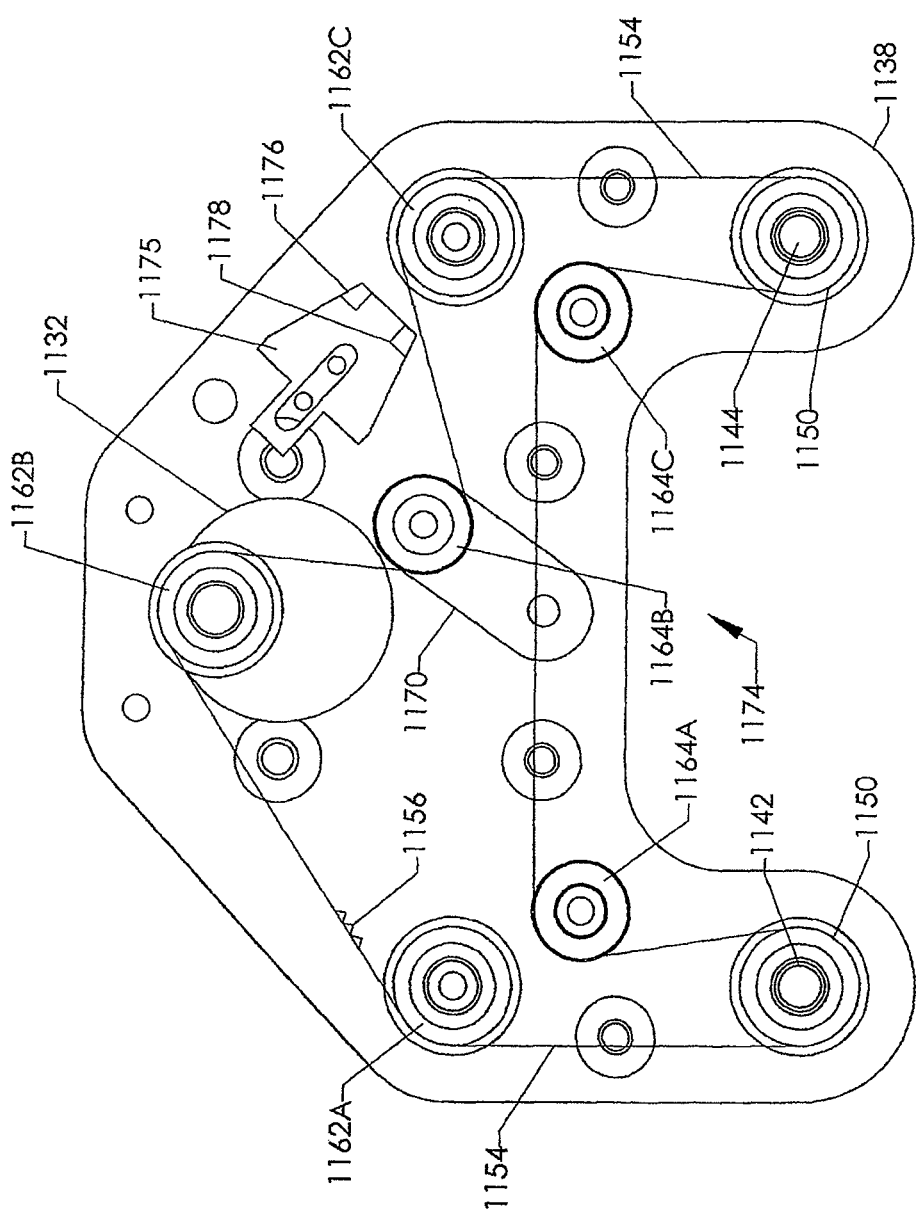
FIG. 11 illustrates a side or end view of the external adjustment device of FIG. 10.

As seen in FIGS. 10 and 11, rotational movement of the pulley 1162B causes the drive belt 1154 to move around the various pulleys 1150, 1162A, 1162B, 1162C and rollers 1164A, 1164B, 1164C. In this regard, rotational movement of the motor 1132 is translated into rotational movement of the two permanent magnets 1134, 1136 via the drive transmission 1160. In one aspect of the invention, the base members 1138, 1140 are cut so as to form a recess 1174 that is located between the two magnets 1134, 1136. During use, the external adjustment device 1130 is pressed against the skin of a patient, or against the clothing which covers the skin (e.g., the external adjustment device 1130 may be used through clothing so the patient may not need to undress). A small permanent magnet may be placed on the patient's clothing to determine the location of the implanted permanent magnet 254 (via the attraction of the two magnets). The recess 1174 allows skin as well as the underlying tissue to gather or compress within the recessed region 1174 as seen in FIGS. 13A and 13B. This advantageously reduces the overall distance between the external drive magnets 1134, 1136 and the permanent magnet 254 contained within the magnetic assembly 236 of the distraction device 200. By reducing the distance, this means that the externally located magnets 1134, 1136 and/or the internal magnet 1064 may be made smaller. This is especially useful in the case of an obese patient.

In one embodiment, the two permanent magnets 1134, 1136 are configured to rotate at the same angular velocity. In another embodiment, the two permanent magnets 1134, 1136 each have at least one north pole and at least one south pole, and the external adjustment device 1130 is configured to rotate the first magnet 1134 and the second magnet 1136 such that the angular location of the at least one north pole of the first magnet 1134 is substantially equal to the angular location of the at least one south pole of the second magnet 1136 through a full rotation of the first and second magnets 1134, 1136.

FIGS. 13A and 13B illustrate cross-sectional views of the patient having an implanted distraction device (not shown for sake of clarity) with a permanent magnet 254 contained within a magnetic assembly 236 (not shown in FIGS. 13A and 13B for clarity sake). The internal permanent magnet 254 is seen disposed on one side of a vertebra 1185. Further, the internal permanent magnet 254 is seen being outside or external with respect to the fascia 1184 and muscle 1186 of the subject. FIGS. 13A and 13B illustrate an obese patient in which skin and other tissue gather within the recess 1174. It should be understood that obese Adolescent Idiopathic Scoliosis patients are rare, and FIGS. 13A and 13B generally indicate a worst-case situation but as seen in FIGS. 13A and 13B the excess skin and other tissue are easily accommodated within the recess 1174 to enable close positioning between the internal permanent magnet 254 and the external drive magnets 1134, 1136. For most AIS patients, the air gap or distance between the internal permanent magnet 254 and the external drive magnets 1134, 1136 is generally one inch or less. In FIGS. 13A through 13D, the internal permanent magnet 254 is depicted somewhat larger than its actual size in order for its respective poles to be more clearly visible.

Still referring to FIGS. 10 and 11, the external adjustment device 1130 preferably includes an encoder 1175 that is used to accurately and precisely measure the degree of movement (e.g., rotational) of the external magnets 1134, 1136. In one embodiment, an encoder 1175 is mounted on the base member 1138 and includes a light source 1176 and a light receiver 1178. The light source 1176 may includes a LED which is pointed or directed toward pulley 1162C. Similarly, the light receiver 1178 may be directed toward the pulley 1162C. The pulley 1162C includes a number of reflective markers 1177 regularly spaced about the periphery of the pulley 1162C. Depending on the rotational orientation of the pulley 1162C, light is either reflected or not reflected back onto the light receiver 1178. The digital on/off signal generated by the light receiver 1178 can then be used to determine the rotational speed and displacement of the external magnets 1134, 1136.

FIGS. 13A, 13B, 13C, and 13D illustrate the progression of the external magnets 1134, 1136 and the internal permanent magnet 254 that is located within the distraction device 200 during use. FIGS. 13A, 13B, 13C, and 13D illustrate the external adjustment device 1130 being disposed against the external surface of the patient's skin 1180 adjacent the spine. In the non-invasive adjustment procedure depicted, the patient 100 lies in a prone position, and the external adjustment device 1130 is placed upon the patient's back. However, the adjustment is conceived possible with the patient in supine, standing or positions. The external adjustment device 1130 is placed against the skin 1180 in this manner to remotely rotate the internal permanent magnet 254. As explained herein, rotation of the internal permanent magnet 254 causes rotational movement of the magnetic assembly 236. This rotational movement is then translated to the lead screw 260 via the locking pin 238 that connects the lead screw 260 to the magnetic assembly 236. Depending on the rotational direction of the lead screw 260, the distraction rod 206 moves in a telescopic manner out of or into the adjustable portion 208. In this regard, by controlling the rotational movement of the magnetic assembly 236 using the external adjustment device 1130, the operator is able to adjust the linear motion of the distraction rod 206 in a controllable manner. The magnetic assembly 236 may have rotational movement though less than 360° of a full rotation of the magnetic assembly 236. Alternatively, the magnetic assembly 236 may have rotational movement through more than 360° (e.g., multiple, full revolutions).

As seen in FIGS. 13A, 13B, 13C, and 13D, the external adjustment device 1130 may be pressed down on the patient's skin 1180 with some degree of force such that skin 1180 and other tissue such as the underlying layer of fat 1182 are pressed or forced into the recess 1174 of the external adjustment device 1130. FIGS. 13A, 13B, 13C, and 13D show the magnetic orientation of the internal permanent magnet 254 as it undergoes a full rotation in response to movement of the permanent magnets 1134, 1136 of the external adjustment device 1130.

With reference to FIG. 13A, the internal permanent magnet 254 is shown being oriented with respect to the two permanent magnets 1134, 1136 via an angle $\theta$. This angle $\theta$ may depend on a number of factors including, for instance, the separation distance between the two permanent magnets 1134, 1136, the location or depth of where the implantable interface 1104 is located, the degree of force at which the external adjustment device 1130 is pushed against the patient's skin. Generally in applications including some obese patients, the angle $\theta$ should be at or around 90° to achieve maximum drivability (e.g., torque). The inventors have calculated that in the AIS application, where there are few obese patients, an angle of about 70° is preferred for the majority of patients when the permanent magnets 1134, 1136 have an outer diameter of about two (2.0) to three (3.0) inches.

FIG. 13A illustrates the initial position of the two permanent magnets 1134, 1136 and the internal permanent magnet 254. This represents the initial or starting location (e.g., 0° position as indicated). Of course, it should be understood that, during actual use, the particular orientation of the two permanent magnets 1134, 1136 and the internal permanent magnet 254 will vary and not likely will have the starting orientation as illustrated in FIG. 13A. In the starting location illustrated in FIG. 13A, the two permanent magnets 1134, 1136 are oriented with their poles in an N-S/S-N arrangement. The internal permanent magnet 254 is, however, oriented generally perpendicular to the poles of the two permanent magnets 1134, 1136.

FIG. 13B illustrates the orientation of the two permanent magnets 1134, 1136 and the internal permanent magnet 254 after the two permanent magnets 1134, 1136 have rotated through 90°. The two permanent magnets 1134, 1136 rotate in the direction of arrow A (e.g., clockwise) while the internal permanent magnet 254 rotates in the opposite direction (e.g., counter clockwise) represented by arrow B. It should be understood that the two permanent magnets 1134, 1136 may rotate in the counter clockwise direction while the internal permanent magnet 254 may rotate in the clockwise direction. Rotation of the two permanent magnets 1134, 1136 and the internal permanent magnet 254 continues as represented by the 180° and 270° orientations as illustrated in FIGS. 13C and 13D. Rotation continues until the starting position) (0° is reached again.

During operation of the external adjustment device 1130, the permanent magnets 1134, 1136 may be driven to rotate the internal permanent magnet 254 through one or more full rotations in either direction to increase or decrease distraction of the distraction device 200 as needed. Of course, the permanent magnets 1134, 1136 may be driven to rotate the internal permanent magnet 254 through a partial rotation as well (e.g., ¼, ⅛, ¹⁄₁₆, etc.). The use of two magnets 1134, 1136 is preferred over a single external magnet because the internal permanent magnet 254 may not be oriented perfectly at the start of rotation, so one external magnet 1134, 1136 may not be able to deliver its maximum torque, which depends on the orientation of the internal permanent magnet 254 to some degree. However, when two (2) external magnets (1134, 1136) are used, one of the two 1134 or 1136 will have an orientation relative to the internal permanent magnet 254 that is better or more optimal than the other. In addition, the torques imparted by each external magnet 1134, 1136 are additive. In prior art magnetically driven devices, the external driving device is at the mercy of the particular orientation of the internal driven magnet. The two-magnet embodiment described herein is able to guarantee a larger driving torque—as much as 75% more than a one-magnet embodiment in the AIS application—and thus the internal permanent magnet 254 can be designed smaller in dimension, and less massive. A smaller internal permanent magnet 254 will have a smaller image artifact when performing MRI (Magnetic Resonance Imaging), especially important when using pulse sequences such as gradient echo, which is commonly used in breast imaging, and leads to the largest artifact from implanted magnets. In certain configurations, it may even be optimal to use three or more external magnets, including one or more magnets each on two different sides of the body (for example front and back).

Figure 14:
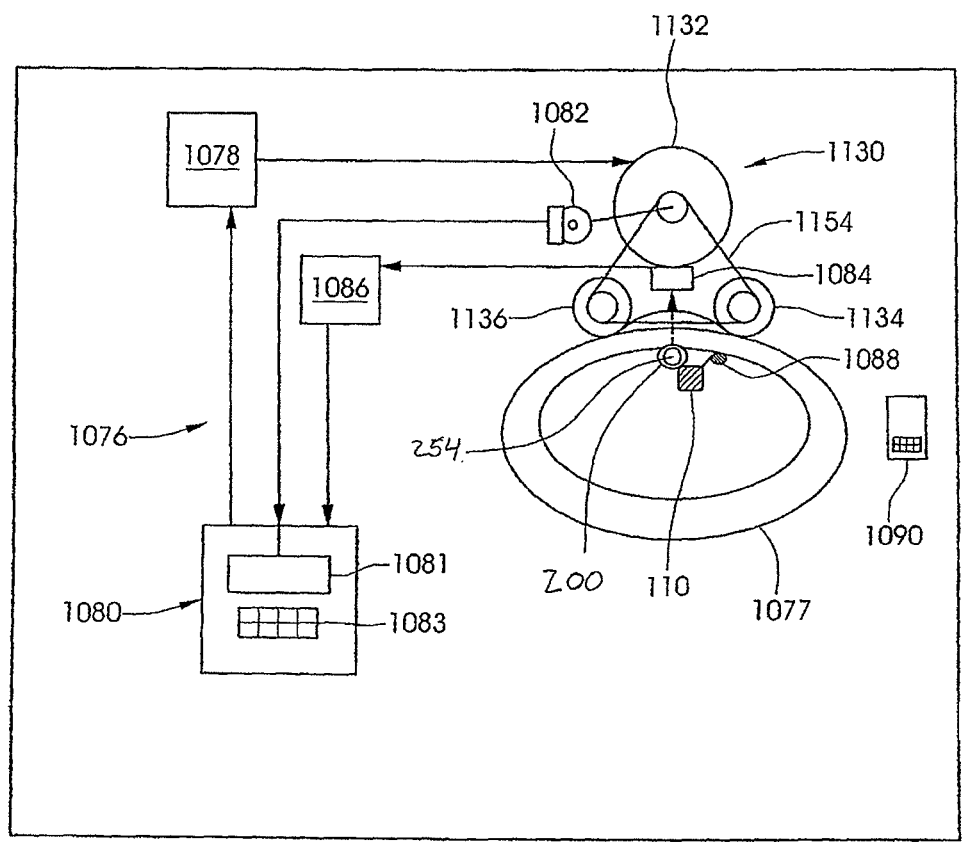
FIG. 14 schematically illustrates a system for driving the external adjustment device according to one embodiment.

FIG. 14 illustrates a system 1076 according to one aspect of the invention for driving the external adjustment device 1130. FIG. 14 illustrates the external adjustment device 1130 pressed against the surface of a patient 1077 (torso face down shown in cross-section). The portion of the distraction device 200 containing the internal permanent magnet 254 is illustrated. The permanent magnet 254 that is located within the magnetic assembly 236 (disposed internally within the patient 1077 is magnetically coupled through the patient's skin and other tissue to the two external magnets 1134, 1136 located in the external adjustment device 1130. As explained herein, one rotation of the external magnets 1134, 1136 causes a corresponding single rotation of the magnetic assembly 236 (which contains the permanent magnet 254). Turning magnetic assembly 236 in one direction causes the distraction device 200 to lengthen, or increase distraction force while turning in the opposite direction causes the distraction device 200 to shorten, or decrease distraction force. Changes to the distraction device 200 are directly related to the number of turns of the magnetic assembly 236.

The motor 1132 of the external adjustment device 1130 is controlled via a motor control circuit 1078 operatively connected to a programmable logic controller (PLC) 1080. The PLC 1080 outputs an analog signal to the motor control circuit 1078 that is proportional to the desired speed of the motor 1132. The PLC 1080 may also select the rotational direction of the motor 1132 (i.e., forward or reverse). In one aspect, the PLC 1080 receives an input signal from a shaft encoder 1082 that is used to identify with high precision and accuracy the exact relative position of the external magnets 1134, 1136. For example, the shaft encoder 1082 may be an encoder 1175 as described in FIGS. 10-11. In one embodiment, the signal is a pulsed, two channel quadrature signal that represents the angular position of the external magnets 1134, 1136. The PLC 1080 may include a built in screen or display 1081 that can display messages, warnings, and the like. The PLC 1080 may optionally include a keyboard 1083 or other input device for entering data. The PLC 1080 may be incorporated directly into the external adjustment device 1130 or it may be a separate component that is electrically connected to the main external adjustment device 1130.

In one aspect of the invention, a sensor 1084 is incorporated into the external adjustment device 1130 that is able to sense or determine the rotational or angular position of the internal permanent magnet 254. The sensor 1084 may acquire positional information using, for example, sound waves, ultrasonic waves, light, radiation, or even changes or perturbations in the magnetic or electromagnetic field between the internal permanent magnet 254 and the external magnets 1134, 1136. For example, the sensor 1084 may detect photons or light that is reflected from the internal permanent magnet 254 or a coupled structure (e.g., rotor) that is attached thereto. For example, light may be passed through the patient's skin and other tissue at wavelength(s) conducive for passage through tissue. Portions of the internal permanent magnet 254 or associated structure may include a reflective surface that reflects light back outside the patient as the internal permanent magnet 254 moves. The reflected light can then be detected by the sensor 1084 which may include, for example, a photodetector or the like.

In another aspect, the sensor 1084 may operate on the Hall effect, wherein two additional magnets are located within the implantable assembly. The additional magnets move axially in relation to each other as the internal permanent magnet 254 rotates and therefore as the distraction increases or decreases, allowing the determination of the current size of the restriction device.

In the embodiment of FIG. 14, the sensor 1084 is a microphone disposed on the external adjustment device 1130. For instance, the microphone sensor 1084 may be disposed in the recessed portion 1174 of the external adjustment device 1130. The output of the microphone sensor 1084 is directed to a signal processing circuit 1086 that amplifies and filters the detected acoustic signal. In this regard, the acoustic signal may include a "click" or other noise that is periodically generated by rotation of the internal permanent magnet 254. For example, the internal permanent magnet 254 may click every time a full rotation is made. The pitch (frequency) of the click may differ depending on the direction of rotation. For example, rotation in one direction (e.g., lengthening) may produce a low pitch while rotation in the other direction (e.g., shortening) may produce a higher pitch signal (or vice versa). The amplified and filtered signal from the signal processing circuit 1086 can then pass to the PLC 1080. Additional details regarding the operation of various acoustic and other detection modalities may be found in U.S. patent application Ser. No. 12/121,355.

During operation of the system 1076, each patient will have a number or indicia that correspond to the adjustment setting or size of their distraction device 200. This number can be stored on an optional storage device 1088 (as shown in FIG. 14) that is carried by the patient (e.g., memory card, magnetic card, or the like) or is integrally formed with the distraction device 200. For example, a RFID tag 1088 implanted either as part of the system or separately may be disposed inside the patient (e.g., subcutaneously or as part of the device) and can be read and written via an antenna 1090 to update the current size of the distraction device 200. In one aspect, the PLC 1080 has the ability to read the current number corresponding to the size or setting of the distraction device 200 from the storage device 1088. The PLC 1080 may also be able to write the adjusted or more updated current size or setting of the distraction device 200 to the storage device 1088. Of course, the current size may recorded manually in the patient's medical records (e.g., chart, card or electronic patient record) that is then viewed and altered, as appropriate, each time the patient visits his or her physician.

The patient, therefore, carries their medical record with them, and if, for example, they are in another location, or even country, and need to be adjusted, the RFID tag 1088 has all of the information needed. Additionally, the RFID tag 1088 may be used as a security device. For example, the RFID tag 1088 may be used to allow only physicians to adjust the distraction device 200 and not patients. Alternatively, the RFID tag 1088 may be used to allow only certain models or makes of distraction devices to be adjusted by a specific model or serial number of external adjustment device 1130.

In one aspect, the current size or setting of the distraction device 200 is input into the PLC 1080. This may be done automatically or through manual input via, for instance, the keyboard 1083 that is associated with the PLC 1080. The PLC 1080 thus knows the patient's starting point. If the patient's records are lost, the length of the distraction device may be measured by X-ray and the PLC 1080 may be manually programmed to this known starting point.

The external adjustment device 1130 is commanded to make an adjustment. This may be accomplished via a pre-set command entered into the PLC 1080 (e.g. "increase distraction displacement of distraction device 200 by 0.5 cm" or "increase distraction force of distraction device 200 to 20 pounds"). The PLC 1080 configures the proper direction for the motor 1132 and starts rotation of the motor 1132. As the motor 1132 spins, the encoder 1082 is able to continuously monitor the shaft position of the motor directly, as is shown in FIG. 14, or through another shaft or surface that is mechanically coupled to the motor 1132. For example, the encoder 1082 may read the position of markings 1177 located on the exterior of a pulley 1162C like that disclosed in FIG. 10. Every rotation or partial rotation of the motor 1132 can then be counted and used to calculate the adjusted or new size or setting of the distraction device 200.

The sensor 1084, which may include a microphone sensor 1084, may be monitored continuously. For example, every rotation of the motor 1132 should generate the appropriate number and pitch of clicks generated by rotation of the permanent magnet inside the distraction device 200. If the motor 1132 turns a full revolution but no clicks are sensed, the magnetic coupling may have been lost and an error message may be displayed to the operator on a display 1081 of the PLC 1080. Similarly, an error message may be displayed on the display 1081 if the sensor 1084 acquires the wrong pitch of the auditory signal (e.g., the sensor 1084 detects a shortening pitch but the external adjustment device 1130 was configured to lengthen).

While embodiments of the present invention have been shown and described, various modifications may be made without departing from the scope of the present invention. The invention, therefore, should not be limited, except to the following claims, and their equivalents.

What is claimed is:

1. A non-invasive adjustable distraction system comprising:
    a distraction rod having a first end, a second end, and a sealable length disposed between the first end and the second end, the first end being configured for affixation to a subject's skeletal system at a first location, the second end comprising a threaded portion;
    an adjustable portion configured for placement relative to the subject's skeletal system at a second location remote from the first location, the adjustable portion comprising a housing containing a magnetic assembly and a threaded screw, the magnetic assembly being rotationally and pivotably coupled to the threaded screw thereby permitting play between the threaded screw and the threaded portion, the threaded screw operatively coupled to the threaded portion of the distraction rod, wherein rotation of the magnetic assembly axially moves the distraction rod relative to the housing;
    a recess disposed in an interior surface of the housing adjacent to one end thereof, the recess defining a volume;
    an annular seal disposed within the recess, the annular seal having an uncompressed volume and a radial thickness;
    wherein the annular seal fills a volume of less than 75% of the volume of the recess in the uncompressed state and wherein the radial thickness of the annular seal is configured to be compressed by greater than 7% when the annular seal is compressed between the recess and a portion of the sealable length of the distraction rod.

2. The distraction system of claim 1, wherein the annular seal fills a volume of between 40% and 54% of the volume of the recess in the uncompressed state.

3. The distraction system of claim 1, wherein the radial thickness of the annular seal is configured to be compressed by between 13% and 18% when the annular seal is compressed between the recess and a portion of the sealable length of the distraction rod.

4. The distraction system of claim 1, wherein the annular seal comprises an o-ring.

5. The distraction system of claim 1, wherein the annular seal comprises ethylene propylene diene M-class rubber.

6. The distraction system of claim 1, wherein the annular seal is formed from a biocompatible rubber having a durometer of around 70.

7. The distraction system of claim 1, further comprising a biocompatible lubricant disposed on the annular seal.

8. The distraction system of claim 1, wherein at least one of the surfaces defining the recess is configured with a surface finish of around 16 microinches RMS or less.

9. The distraction system of claim 1, wherein an interior of the housing is configured to maintain positive air pressure post-implantation.

10. A non-invasive adjustable distraction system comprising:
    a distraction rod having a first end, a second end, and a sealable length disposed between the first end and the second end, the first end being configured for affixation to a subject's skeletal system at a first location, the second end comprising a threaded portion;
    an adjustable portion configured for placement relative to the subject's skeletal system at a second location remote from the first location, the adjustable portion comprising a housing containing a magnetic assembly and a threaded screw, the magnetic assembly being rotationally and pivotably coupled to the threaded screw thereby permitting play between the threaded screw and the threaded portion, the threaded screw operatively coupled to the threaded portion of the distraction rod, wherein rotation of the magnetic assembly axially moves the distraction rod relative to the housing;
    a gland secured to one end of the housing, the gland containing therein a recess defining a volume wherein the recess is disposed on an interior surface of the gland;
    an annular seal disposed within the recess, the annular seal having an uncompressed volume and a radial thickness;
    wherein the annular seal fills a volume of less than 75% of the volume of the recess in the uncompressed state and wherein the radial thickness of the annular seal is configured to be compressed by greater than 7% when the annular seal is compressed between the recess and a portion of the sealable length of the distraction rod.

11. The distraction system of claim 10, wherein an internal diameter of the gland is less than an inner diameter of the housing.

12. The distraction system of claim 10, wherein the housing comprises a tubular housing.

13. The distraction system of claim 10, wherein the annular seal fills a volume of between 40% and 54% of the volume of the recess in the uncompressed state.

14. The distraction system of claim 10, wherein the radial thickness of the annular seal is configured to be compressed by between 13% and 18% when the annular seal is compressed between the recess and a portion of the sealable length of the distraction rod.

* * * * *

UNITED STATES PATENT AND TRADEMARK OFFICE
CERTIFICATE OF CORRECTION

PATENT NO. : 8,974,463 B2  
APPLICATION NO. : 13/477945  
DATED : March 10, 2015  
INVENTOR(S) : Pool et al.

It is certified that error appears in the above-identified patent and that said Letters Patent is hereby corrected as shown below:

In the specification

Column 4 line 50, Change "envelope a." to --envelope $\alpha$.--.

In the claims

Column 18 line 33 Claim 10, Change "volume" to --volume,--.

Signed and Sealed this  
Twenty-ninth Day of December, 2015

Michelle K. Lee  
*Director of the United States Patent and Trademark Office*